(12) United States Patent
Nielsen et al.

(10) Patent No.: US 7,541,817 B2
(45) Date of Patent: Jun. 2, 2009

(54) METHOD AND A SYSTEM OF DIAGNOSING CORROSION RISK OF A PIPE OR A PIPELINE IN SOIL

(75) Inventors: Lars V. Nielsen, Rodovre (DK); Folke Galsgaard, Niva (DK)

(73) Assignee: Metricorr APS, Rodovre (DK)

( * ) Notice: Subject to any disclaimer, the term of this patent is extended or adjusted under 35 U.S.C. 154(b) by 0 days.

(21) Appl. No.: 10/591,226

(22) PCT Filed: Mar. 1, 2005

(86) PCT No.: PCT/DK2005/000142

§ 371 (c)(1),
(2), (4) Date: Jun. 11, 2007

(87) PCT Pub. No.: WO2005/083392

PCT Pub. Date: Sep. 9, 2005

(65) Prior Publication Data

US 2008/0036476 A1 Feb. 14, 2008

(30) Foreign Application Priority Data

Mar. 1, 2004 (EP) .................................. 04388014

(51) Int. Cl.
*G01R 27/08* (2006.01)
(52) U.S. Cl. ......................... 324/700; 324/635; 324/444; 324/71.2; 205/775.5; 166/250.05; 392/457
(58) Field of Classification Search .................. 324/700
See application file for complete search history.

(56) References Cited

U.S. PATENT DOCUMENTS

| | | | | |
|---|---|---|---|---|
| 5,389,216 A | * | 2/1995 | Balkanli | ................... 205/775.5 |
| 5,404,104 A | | 4/1995 | Rivola et al. | |
| 5,821,742 A | * | 10/1998 | Carr et al. | ..................... 324/74 |
| 6,160,403 A | | 12/2000 | Kajiyama | |
| 6,359,434 B1 | * | 3/2002 | Winslow et al. | ............. 324/220 |
| 6,774,814 B2 | * | 8/2004 | Hilleary | ................. 340/870.07 |
| 6,936,158 B2 | | 8/2005 | Nielsen et al. | |

(Continued)

FOREIGN PATENT DOCUMENTS

GB 2064124 6/1981

*Primary Examiner*—Timothy J Dole
*Assistant Examiner*—Benjamin M Baldridge
(74) *Attorney, Agent, or Firm*—Klein, O'Neill & Singh, LLP

(57) ABSTRACT

A method of diagnosing corrosion risk of a buried pipe due to DC stray currents and/or AC voltages induced in soil employs a metal probe including a first, exposed part having a first specific resistivity, and a second, sealed reference part having a second specific resistivity. The probe is buried in the soil, and the AC current and voltage between the pipe and the probe are measured, from which the spread resistance is determined. The resistances of the first and second probe parts are determined by respectively passing first and second excitation currents through the first and second probe parts and measuring the voltages across them. The resistance measurements are stored, and the steps are repeated periodically. The corrosion of the first probe part is determined from the measurements according to an algorithm, and the pipe corrosion risk is diagnosed from an empirical combination of the corrosion of the first probe part, the spread resistance, and the AC voltage measured.

11 Claims, 7 Drawing Sheets

U.S. PATENT DOCUMENTS

2003/0006148 A1* 1/2003 Nielsen et al. ........... 205/775.5
2003/0169058 A1* 9/2003 Pierre et al. ................. 324/700
2004/0232924 A1* 11/2004 Hilleary et al. ............. 324/700
2008/0260324 A1* 10/2008 Takahashi et al. ............. 385/12

* cited by examiner

METHOD AND A SYSTEM OF DIAGNOSING CORROSION RISK OF A PIPE OR A PIPELINE IN SOIL

CROSS-REFERENCE TO RELATED APPLICATIONS

This application is the national phase, under 35 U.S.C. §371(c), of PCT/DK2005/000142, filed 1 Mar. 2005, the disclosure of which is incorporated herein by reference.

FEDERALLY SPONSORED RESEARCH OR DEVELOPMENT

Not Applicable

BACKGROUND OF THE INVENTION

The present invention relates to detection of corrosion of cathodically protected, CP, buried pipelines by use of probes buried in the soil adjacent to the pipelines and electrically connected to the pipelines. More specific, the invention relates to detection of corrosion caused by the combined effect of specific soil parameters and electric fields such as DC stray current or AC voltage induced as a result of paralleling the pipeline with high voltage power lines. Such corrosion is sometimes found to proceed although measures have been taken to eliminate the corrosion effects, e.g. by imposing DC current to the pipeline by an external electrode and a rectifier system, or by sacrificial anodes coupled to the pipe. Usual acceptance criteria (safe/not safe with regard to corrosion) are built upon the DC potential of the pipeline, but specifically in the case of AC induced corrosion, these criteria are not reliable.

Related apparatuses and techniques are described in publications such as US 2003/006148, GB 2 064 124, EP 0 882 975, EP 0 560 443 and EP 1 152 235. Preference is made to all of the above mentioned patent publications and all are hereby incorporated the present specification by reference.

SUMMARY OF THE INVENTION

In a first aspect, the present invention relates to a method of diagnosing corrosion risk of a pipe or a pipeline buried in soil due to DC stray currents and/or AC voltages induced in the soil, the method may comprise:
i) providing a two-part metal probe including a first probe part having a first metal element of a first size and a first specific resistivity, the first probe part constituting an exposed element, and a second probe part having a second metal element of a second size and a second specific resistivity, the second probe part being hermetically sealed and constituting a reference element,
ii) burying the two-part metal probe in the soil,
iii) measuring the AC current flowing between the pipe or the pipeline and the two-part metal probe,
iv) measuring the AC voltage between the pipe or the pipeline and the two-part metal probe,
v) measuring the spread resistance based on the AC current determined in step iii) and the AC voltage measured in step iv) according to Ohm's Law,
vi) passing a first excitation current through the first probe part and determining the voltage generated by the first excitation current across the first probe part for measuring the resistance of the first probe part according to Ohm's Law,
vii) passing a second excitation current through the second probe part and determining the voltage generated by the second excitation current across the second probe part for measuring the resistance of the second probe part according to Ohm's Law,
viii) storing the measurements provided in steps iii), iv), v), vi) and vii),
ix) repeating the steps iii), iv), v), vi), vii) and viii) periodically,
x) determining the corrosion of the first probe part based on the measurements performed in steps vi) and vii) according to a mathematical corrosion algorithm, and
xi) diagnosing the risk of corrosion of the pipe or pipeline based on an empirical combination of the actual corrosion of the first probe part, the spread resistance determined in step v) and the AC voltage measured in step iv).

The two-part metal probe may be buried in the soil at or near the pipe or pipeline.

A second aspect of the present invention relates to a system of diagnosing corrosion risk of a pipe or a pipeline buried in soil due to DC stray currents and/or AC voltages induced in the soil, comprising:
i) a two-part metal probe including a first probe part having a first metal element of a first size and a first specific resistivity, the first probe part constituting an exposed element, and a second probe part having a second metal element of a second size and a second specific resistivity, the second probe part being hermetically sealed and constituting a reference element, and having a cable for connection to an external measuring apparatus,
ii) a measuring apparatus including
a housing,
a cable connector for the connection of the cable of the two-part metal probe to the external measuring apparatus included within the housing,
an AC current measuring circuit for measuring the AC current flowing between a pipe or pipeline and the two-part metal probe when the probe is buried in the soil,
an AC voltage measuring circuit for measuring the AC voltage between the pipe or the pipeline and the two-part metal probe when the two-part metal probe is buried within the soil,
a resistance measuring circuit connected to the AC current measuring circuit and the AC voltage measuring circuit for determining the spread resistance based on Ohm's Law,
a current excitation circuit for passing through the cable a first excitation current to the first probe part and for measuring the voltage generated by the first excitation current across the first probe part for measuring the resistance of the first probe part according to Ohm's Law and for passing a second excitation current through the cable to the second probe part and for determining the voltage generated by the second excitation current across the second probe part for measuring the resistance of the second probe part according to Ohm's Law,
storage means for storing the measurements made by the AC current measuring circuit, the AC voltage measuring circuit, the spread resistance measuring circuit and the current excitation circuit, and a diagnosing circuit for diagnosing the risk of corrosion of the pipe or pipeline based on an empirical combination of the actual corrosion of the first probe part, the spread resistance and the AC voltage.

A path of communication may be established between the probe and the apparatus for enabling the apparatus to conduct measurements. The two-part metal probe and the apparatus are preferably inter-connected by a cable. The cable may be of a multi-lead type, such as a cable having two or more wires.

A third aspect of the present invention relates to a two-part metal probe for use in carrying out the method according to the first aspect and for use in the system according to the second aspect and including a first probe part having a first metal element of a first size and a first specific resistivity, the first probe part constituting an exposed element, and a second probe part having a second metal element of a second size and a second specific resistivity, the second probe part being hermetically sealed and constituting a reference element.

A fourth aspect of the present invention relates to a measuring apparatus for use in carrying out the method according to the first aspect and constituting a part of the system according to the second aspect. The measuring apparatus according to the fourth aspect of the present invention preferably at least constitutes the entire measurement apparatus part of the system according to the second aspect of the present invention but may also constitute a limited part thereof.

Generally, instant corrosion rates are determined by applying electrochemical techniques such as electrochemical impedance spectroscopy (EIS), linear polarisation resistance (LPR) or electrochemical noise (EN) measurements. However, since these techniques require a conducting electrolyte system e.g. a stable water phase they are not applicable in a corrosion process when water is not continuously present. Further, even though the requirements for performing electrochemical measurements are present inaccurate results may occur induced by additional current responses from redox-processes other than those involved in the particular corrosion process, which additional current responses may superimpose on the current response from the corrosion process and cause inaccurate or misleading results. In addition, the interpretation of the results of a measurement performed using one of the generally applied electrochemical techniques often require a specific expertise and knowledge of the user.

Accumulated corrosion is generally quantified by, weight loss measurements, ultrasonic based thickness measurements, eddy-current techniques in near field and far field, magnetic flux leakage techniques or visual inspections (microscopy). In addition, a monitoring of accumulated corrosion in process plants commonly utilizes measurements of electrical resistance (ER) of a corroding metal wire placed in a probe, ER technique. All of the above mentioned techniques for determining accumulated corrosion generally require a series of measurements to be performed with regular time intervals (years, months, weeks or days) after which the individual measurements may be compared and translated into a degree of accumulated corrosion. None of the techniques provide a fast measurement of instant rate of corrosion or in other words the resolution of these techniques is insufficient. However, thin metal plates have been incorporated in commercial ER-probes and applied in process plants to follow the efficiency of corrosion inhibitor dosage with a fairly quick response (days, weeks or months depending on the actual corrosion rate).

The electrical resistance (ER) technique often utilizes a Wheatstone bridge circuit for the comparison of the electrical resistance of a test section or coupon exposed to a hostile environment and the electrical resistance of a reference coupon protected against the hostile environment. By repeating measurement at regular time intervals, e.g. on a weekly or monthly basis, the accumulated corrosion may be followed throughout time. To achieve acceptable results from a series of measurements reflecting the degree of accumulated corrosion, the applied ER-technique must measure the resistance of the test coupon and the resistance of the reference coupon accurately. However, the resistance of the test coupon and the resistance of the reference coupon are highly temperature dependent. Consequently, the effect of temperature variations from one measurement to another will cause unwanted inaccuracies in the measurements and decreases the comparability of the individual measurements included in a series of measurements.

The probability of corrosion of buried metallic structures may be assessed from formula's found in standards such as the German standard DIN 929 or similar standards. According to the German standard, the soil aggressiveness is based on a type of soil, the soil homogeneity, the resistivity of the soil, the water content of the soil, the pH value, the buffer capacity, the sulfide concentration, the neutral salt contents, the sulfate content, as well as the location of the metallic structure with respect to ground water. A rating is assigned each of these parameters and a total rating is calculated and used for assessment of the probability of corrosion.

Since pipelines are running long distance and through a variety of soil conditions, the protection of the pipe from corrosion is necessary in order to prevent or at least delay the generation of leaks. Typically, this protection is made primarily by coating the pipeline, which insulates the pipeline from the adjacent environment. Since coating faults and defects, such as coating pinholes or coating imperfections, are unavoidable, the pipe or pipeline is usually further protected from corrosion by applied cathodic protection. The CP or cathodic protection may be obtained either by impressed current using a rectifier and an anode bed system or by use of sacrificial anodes. The cathodic protection controls the pipe to soil potential to a safe region.

An exchange of alternating current is possible between the soil and the bare metal at coating defects on metallic structures. This applies particularly to carbon steel pipelines for which the level of AC can be significant in the proximity of high voltage electrical power lines, power stations, or traction systems.

A preliminary European Standard prEN 50162 on protection against corrosion by stray current from direct current systems is intended to offer guidance for design of direct current systems which may produce stray currents; for design of metal structures, which are to be buried or immersed, and which may be subject to stray current corrosion; and for the selection of appropriate protection measures.

Table 1 gives the criteria that should be met in order to keep the structure protected from corrosion. The protection potential describes the maximum potential, i.e. in order to keep the structure from corroding, the potential should be kept more negative than the protection potential.

TABLE 1

Free corrosion potentials and protection potentials of non-alloy and low alloy Fe-materials in soil and in fresh and salt water according to the EN 12954 standard on cathodic protection of buried or immersed structures. All measured against the Cu/CuSO4 (CSE) reference electrode.

| Medium | | Free corrosion potential, V CSE | Protection potential (off), V CSE |
|---|---|---|---|
| Water and soil Aerobic conditions | Normal condition | −0.65 to −0.40 | −0.85 |
| | Aerated sandy soil $100 < \rho < 1000 \ \Omega \cdot m$ | −0.50 to −0.30 | −0.75 |
| | Aerated sandy soil $\rho > 1000 \ \Omega \cdot m$ | −0.40 to −0.20 | −0.65 |
| Water and soil Anaerobic conditions | | −0.80 to −0.65 | −0.95 |

According to the EN 12954 standard, structures protected against corrosion by cathodic protection should be deemed to be exposed to unacceptable stray currents if the IR free potential (off potential) is outside the protective potential range defined by EN 12954. Further, to evaluate the acceptability of stray current interference the installation of test probes and coupons should be considered. In situations with fluctuating interference current probe measurements can be used to evaluate the acceptability of interference.

It is suggested that currents measured between the pipe and the hereto connected probe during a 24 hour period should be compared with current flowing in a well protected system without stray current. Accept criteria are based on time at bad condition and the degree of the bad condition. No direct corrosion rate is measured; however weight loss coupons can be used to further verify the well-functioning of the CP system or the degree to which corrosion occurs due to DC stay current interference. Weight loss coupons that are electrically coupled to the pip and exposed in the adjacent soil. The coupons are weighed before such exposure. After an adequate period of time (typically one year or more) the coupons are excavated and brought to the laboratory for cleaning and weighing once again. The weight loss can be used to describe the corrosion. The procedure is rather time consuming and the corrosion condition cannot be detected during the period of exposure, i.e. one has to excavate, bring coupons to the lab and analyze them before the result is evident.

The American National Association of Corrosion Engineers, NACE, also provide standards that are very well respected throughout the world. NACE Standard RP0169 on control of external corrosion on underground or submerged metallic piping systems deals with design, installation and operation and maintenance of anticorrosion measures covering both external coating systems and cathodic protection systems. NACE Standard TM0497 is dealing with measurement techniques related to criteria for cathodic protection on underground or submerged metallic piping systems. The cathodic protection criteria are slightly different from the EN standards defined in table 1, since three acceptance criteria can be used.

TABLE 2

Cathodic protection acceptance criteria according to NACE standard procedures.

| Criterion No | (potentials versus CSE electrode) | Additional conditions and remarks |
|---|---|---|
| 1 | −850 mV or more negative on-potential | Significance of the voltage drop shall be considered, e.g. by comparing historical levels of cathodic protection or soil corrosiveness with physical evidence from the pipeline to determine whether corrosion has occurred. |
| 2 | −850 mV or more negative off-potential | Most commonly used |
| 3 | 100 mV cathodic polarization | Especially useful for bare or ineffectively coated pipe and where corrosion potentials may be low (for example 500 mV or less negative) and/or the current needed to meet the negative 850 mV or more negative polarized potential would be considered excessive. |

A NACE standard recommended practice RP0177 on mitigation of alternating current and lightning effects on metallic structures and corrosion control systems covers personnel safety and protection of equipment rather than deals with the corrosion problem itself. This standard is therefore not considered to be relevant for the detection of AC induced corrosion, but may be useful when the problem has been encountered and measures for mitigation of the problem should be implemented.

However neither the NACE or the EN standards covers satisfactorily the AC corrosion problem. CP criteria are based on potential measurements and these are inadequate for coping with AC interference effects on corrosion.

A set of papers and guidelines that most directly focuses on the AC corrosion problem is the so-called CeoCor Booklet on AC corrosion on cathodically protected pipelines (guidelines for risk assessment and mitigation measures). In this publication, various terms and parameters are discussed regarding their applicability for the AC corrosion detection. In chapter 4 on evaluation of the corrosion risk, it is stated that the likelihood of AC corrosion can be evaluated according to either calculating the induced AC level on the pipelines (guidelines are given) or by measurements on site. According to the teachings of the invention, measurements on site are not avoided by making calculations on the level of AC induced on the pipeline, however, these calculations may come prior to the establishment of test points and equipment.

Regarding the measurements on site, the CeoCor booklet guide suggest a range of simple preliminary indicative measurements, and three specific measurements to be carried out for the purpose of evaluating AC corrosion risk. The specific measurement techniques include three methods as described in table 3.

TABLE 3

The specific measuring techniques and their interpretation according to the CeoCor AC corrosion booklet.

| No. | Parameter | Method | Evaluation of AC corrosion risk |
|---|---|---|---|
| 1 | Pipe to soil potential | A steel coupon with known imperfect surface is installed into the soil close to the pipeline, and electrically connected to the pipeline to undergo the cathodic protection current and the AC interference as the pipeline under investigation. The coupon will allow to polarize. A reference electrode will be placed into the soil as close as possible to the coupon, preferably integrated with the coupon. For measuring purposes the instant off | Using this measuring technique, the pipeline is considered protected from AC corrosion if the coupon to soil off potential is at any moment more negative than the protective potential range (table 1). |

TABLE 3-continued

The specific measuring techniques and their interpretation according to the CeoCor AC corrosion booklet.

| No. | Parameter | Method | Evaluation of AC corrosion risk |
|---|---|---|---|
| | | potential (coupon to soil) may be measured by disconnecting the coupon from the pipeline, measuring the potential without IR drop. To perform the measurement automatically a measuring system may be used. This measuring system consists of an electronic recording device that reads and stores data periodically and desynchronized from the AC interferences. The devise measures the potential when the coupon is connected to the pipeline (on potential), disconnects the coupon from the pipeline then measures the off potential 1 ms after disconnecting, and connects the coupon to the pipeline again. Together with the on potential the current to the coupon is measured and recorded. Approximately 20 ms afterwards, the cycle is repeated. Due to the desynchronization of the measuring cycle from the AC interference, the measurements will be taken at any time within the AC interference period, including peak values. | |
| 2 | AC current density | A steel coupon with known imperfect surface is installed into the soil close to the pipeline, and electrically connected to the pipeline to undergo the cathodic protection current and the AC interference as the pipeline under investigation. An ammeter is introduced in the connecting wire to measure the RMS value of the AC current. Small currents should be measured as the voltage drop on a resistor (1 ohm or less) or by using a zero resistance am-meter. The RMS current density is then calculated. | Using this measuring technique the pipeline is considered protected from AC corrosion if the RMS AC current density is lower than 30 A/m2. |
| 3 | Current density ratio ($J_{AC}/J_{DC}$) | A steel coupon with known imperfect surface is installed into the soil close to the pipeline, and electrically connected to the pipeline to undergo the cathodic protection current and the AC interference as the pipeline under investigation. An ammeter is introduced in the connecting wire to measure the DC and the RMS value of the AC current. Small currents should be measured as the voltage drop on a resistor (1 ohm or less) or by using a zero resistance am-meter. From these values, the ratio $J_{AC}/J_{DC}$ is calculated. | Using this measuring technique, if the RMS AC current density to DC current density ratio: is lower than 3 then the AC corrosion risk is considered to be low is between 3 and 10 the AC corrosion risk is considered to be medium, and further investigation is advised. is higher than 10 the AC corrosion risk is considered to be high and immediate mitigation measures should be taken. |

However, these methods are insufficient and may give false indications. Methods 1 and 3 indicate that AC induced corrosion can be avoided by further increasing the CP dosage of the rectifier system, and this may lead directly to a worsening of the situation. Method 2 may have some reason, however, since most interference patterns involve large variations of the induced AC voltage throughout the day, the method require a logging of the data over at least a 24 h period.

All three methods agree that external coupons are necessary for the evaluation procedure, but none of the methods actually measure the actual corrosion rate on said coupon.

It is further worth noticing that a term known as the spread (or spreading) resistance is defined in the CeoCor booklet.

This indicates the Ohmic resistance from pipe via a coating defect to soil or alternatively the Ohmic resistance from a coupon surface to soil. It depends on the area of the coating defect (or active area of the coupon), and the resistivity of the soil present very close to the surface. Since electrolysis occurs right at the surface, the spread resistance is usually very different from the general soil resistivity further away from the surface. The spread resistance of a coupon is normally measured by inserting a large auxiliary electrode into the soil and using a modification of the Wenner four-pin method using a device as described in ASTM G 57-95A standard on soil resistivity measurements. This method provide an excitation current between the auxiliary electrode and the coupon and measures the voltage such created in the measuring circuit. The frequency of the excitation voltage is large enough to avoid polarization of the electrodes, which normally means >90 Hz.

It is contemplated that this parameter is a very important one, and incorporates a modification of this into the invention as described below.

It is an object of the present invention to provide a novel technique of improved diagnosing corrosion risk of pipes or pipelines buried in soil to specific soil parameters, and electrical fields such as a DC stray current and/or AC voltages induced as a result of paralleling the pipeline with high voltage power lines.

It is an advantage of the present invention that the technique of diagnosing corrosion risk of a pipe or a pipeline buried in soil due to DC stray currents and/or AC voltages induced in the soil may be carried out based on a simple combination of current and voltage measurements and calculating specific resistances in accordance with Ohms's Law for determining reproducible parameters readily combinable according to an empirical scheme for diagnosing the corrosion risk.

The technique according to the present invention involves probes electrically connected to the pipeline, and an instrumentation to be installed in a standard measuring post. In a presently preferred embodiment, the instrumentation may control and store data from three such probes. The probes are buried in the soil and the electrical connection to the pipe is made in the instrumentation positioned (for instance) in the standard measuring post.

The probes constitute typically two (or more) metal elements, most often initially identical, built into an ER (electrical resistance) probe. One element (denoted hereafter the coupon element, C) is exposed in the hostile environment and diminishes in thickness due to corrosion. The resistance of the coupon element (RC) changes primarily with thickness and temperature. A second element (denoted hereafter the reference element, R) is shielded from the hostile environment, e.g. by coating. The resistance of the reference element (RR) changes primarily with temperature and the element is used for compensation of this effect. The probe is used for measurements of the corrosion rate and degree of accumulated corrosion according to procedures e.g. described in previous patent application publication number WO 01/42764.

According to a pre-programmed time schedule, the instrument wakes up and performs a series of measurements on the probe(s). Firstly, the AC current (Iclosed) flowing between the pipe and the individual probe is measured.

Secondly, one probe at a time is disconnected from the pipe, and the AC voltage between the pipe and the probe is measured (Vopen).

Thirdly, in the disconnected condition, the instrumentation measures the resistance of the (two) elements of an ER probe. Excitation current is passed through the elements, and a data acquisition system picks up the voltages generated across the elements and scales this properly into a measure of the element resistances, RC and RR. The electrical connection between the pipe and the probe is then re-established, and the instrumentation continues to address the remaining probes.

For each measurement the following data are stored: Time stamp (t), Vopen (1 to 3) (AC voltage between pipe and probe), Iclosed (1 to 3) (AC current resulting for the AC voltage), RR(t) (channel 1 to 3), RC(t) (channel 1 to 3)

All data are saved in a built-in data logging facility or transferred to a control center.

By data processing means, the resistance values of the ER probe elements are then used to calculate element thickness at time t by a mathematical algorithm, for instance:

$$\sigma(t) = \sigma(t=0) \cdot \frac{R_R(t)}{R_C(t)} \cdot \frac{R_C(t=0)}{R_R(t=0)}$$

where (t=0) refers to initial probe conditions. By comparison with initial element thickness, the degree of accumulated corrosion can be calculated and from the slope of a series of measurements the corrosion rate of the element can be calculated. Temperature drift is eliminated since both elements have the same temperature.

A specific feature of the present invention is therefore to measure corrosion on the probes directly, and not just indicative by selecting electrical parameters (as in the identified standards) that are descriptive of the potential corrosion risk.

The frequency of the electrical parameters Vopen and Iclosed are identical to the frequency AC voltage induced on the pipeline e.g. 50 Hz. These parameters are used in a diagnostic manner to determine if experienced corrosion can be attributed to induced AC voltage or DC stray currents.

The spread resistance (Rspread) of the probe is calculated simply by dividing AC voltage (Vopen) by AC current (Iclosed). The spread resistance is a function of the probe element area, the soil conditions, and the electrolysis occurring directly at the probe surfaces due to electrochemical processes. Multiplying by area of the element, a universal diagnostic parameter can be used to characterise the local conditions at the probe surface. A very high spread resistance is indicative of either dry soil conditions or precipitations of resistive films on the surface. Both these conditions are inhibiting AC induced corrosion. A very low spread resistance is a pre-requisite for AC induced corrosion, and—in combination with high AC voltage and a measurable corrosion rate—can be used to diagnose AC induced corrosion.

A specific feature of the present invention is therefore to compare the corrosion condition or corrosion rate as measured by the ER method with the spread resistance of the probe. This spread resistance is normally measured by insertion of auxiliary electrodes and using separate instrumentation for creating an excitation current between the auxiliary electrode and the probe as described in standard ASTM G 57-95A10 for soil resistivity measurements.

In the present invention, the spread resistance is measured simply by making use of the pipe as the auxiliary electrode and using the (on pipe) induced AC voltage for measuring the AC current and consequently determining the spread resistance in accordance with Ohm's law. The frequency is lower (here 50 Hz, 16⅔ Hz or whatever the frequency of the actually induced AC voltage) than as used in the standard four pin Wenner concept, however, for the purpose of assessing the spread resistance in the region of interest (ranges throughout say 4 decades), a slight polarisation is allowable. Using the frequency actually arising from the voltage on pipe, this version of the spread resistance may even become more relevant than a spread resistance measured according to standard procedures.

Accordingly, the combination of the above-mentioned parameters is very helpful and powerful in diagnosing corrosion risk on one hand and the cause of the corrosion risk on the other hand. The table gives one presently preferred guideline for diagnosing risk of AC induced corrosion.

TABLE 4

| Event | Active corrosion | Spread resistance | AC voltage | Diagnose |
|---|---|---|---|---|
| 1 | no | high (1-10 $\Omega m^2$) | low (below approx. 10 V) | No risk |
| 2 | no | high (1-10 $\Omega m^2$) | high (above approx. 10 V) | No critical condition but monitor spread resistance further |
| 3 | no | low (0.001-0.1 $\Omega m^2$) | low (below approx. 10 V) | No critical condition but be aware of increased AC voltage |
| 4 | no | low (0.001-0.1 $\Omega m^2$) | high (above approx. 10 V) | Risk of AC corrosion incubation period |
| 5 | yes | low (0.001-0.1 $\Omega m^2$) | high (above approx. 10 V) | AC corrosion - take mitigation actions |
| 6 | yes | low (0.001-0.1 $\Omega m^2$) | low (below approx. 10 V) | Corrosion may arise from DC stray current |
| 7 | yes | high (1-10 $\Omega m^2$) | low (below approx. 10 V) | Corrosion may arise from DC stray current |
| 8 | yes | high (1-10 $\Omega m^2$) | high (above approx. 10 V) | Corrosion may arise from DC stray current |

The spread resistance values may be in the region 0.01Ω (0.001Ω) to 10Ω (100Ω), and the AC voltage in between 0 and several hundred volts, however, in the Danish sector, the voltage should be kept below 50 V for human safety reasons. A "high" AC voltage may be as low as e.g. 10 V.

The logging of data should be made so as to detect daily variations in the induced AC voltage, whether this is realised by logging once every hour or by logging e.g. every 24+dt hour, where dt is an amount of time ensuring that measurements eventually are taken and stored for time stamps representing the entire day.

The signal from each of the probes may be converted from analogue to digital signals using a analogue-to-digital converter (ADC) for processing the signals in a digital processing unit such as micro controller or micro processor. ADC's are well known to persons skilled in the art and will not be discussed further.

BRIEF DESCRIPTION OF THE DRAWINGS

The present invention will now be described with reference to the appended figures, wherein.

DETAILED DESCRIPTION OF THE INVENTION

Figure 1:
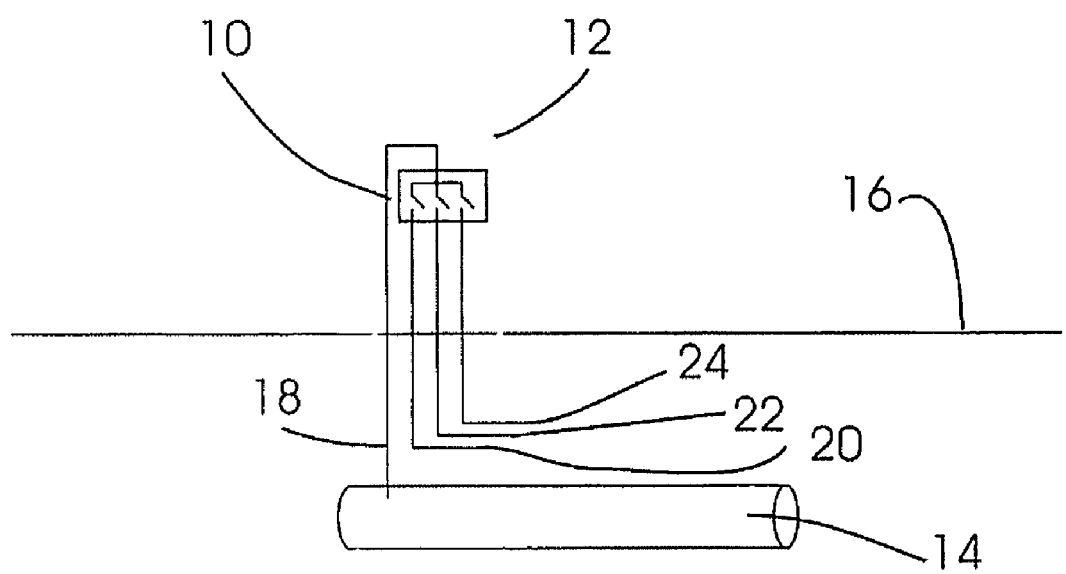
FIG. 1 is a schematic representation of a measurement system according to the present invention.

FIG. 1 illustrates the schematic set-up of the measurement system according to the present invention. The measurement system 10 is placed inside a measuring post 12. Measuring posts are placed along high pressure pipelines such as illustrated by a piece of a pipeline 14 buried beneath the surface of the ground 16. As the pipelines are usually placed along high voltage power lines, the measuring post 12 may also comprise measuring instruments for measuring and monitoring the performers of the high voltage power lines.

The measurement system 10 has at least one electrical connection to the buried pipeline 14 constituted by an electrical wire 18. Buried in the ground, preferably parallel to the pipeline 14 are at least one probe and preferably three probes designated the numerals 20, 22, 24.

The measuring system 10 may also be placed in a specialised post separate from the standard measuring post 12.

Figure 2A:
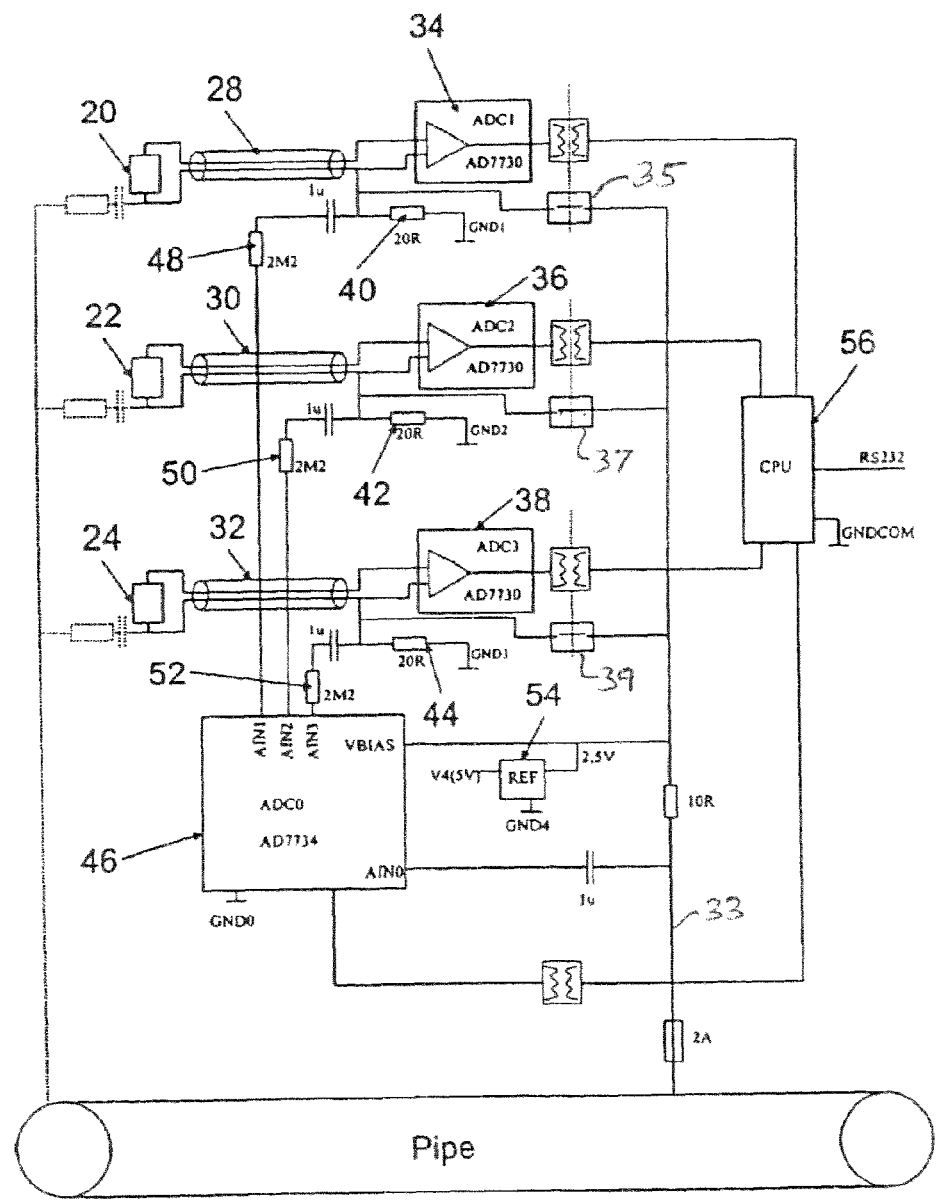
FIG. 2a is a schematic representation of the electrical connections in a measuring system according to the present invention.

FIG. 2a is a schematic representation of the measurement system 10. In the presently preferred embodiment of the present invention, the measurement system 10 is electrically connected to three separate probes 20, 22 and 24, each connected to a processing unit 56. In the presently preferred embodiment of the present invention, each of the sensors 20, 22, 24 is not directly coupled to the processing unit 56. Each of the sensors 20, 22, 24 is connected to a corresponding two sire balanced wire 28, 30, 32, which ensures that external electrical noise only has a minimal influence on the electrical signal travelling through each of the wires 28, 30, 32.

Each of the wires 28, 30, 32 is coupled to a corresponding differential analogue to a digital converter 34, 36, 38. The AD converter converts the analogue signal representing the voltage measured from each of the probes 20, 22 and 24.

Each of the probes 20, 22, 24 is supplied with 5 volts through a 20 ohm reference resistor 40, 42, 44. The common mode current of the probe will be approximately 2.5 volts, which is within the AD converter's common mode region, The probes 20, 22, 24 are connected to the pipeline by a cable 33. The probes 20, 22, 24 are, in turn, electrically connected to the cable 33 through switching 35, 37, 39, respectively. The switching devices 35, 37, 39 are operable for the selective electrical connection and disconnection of the respective probes and the pipline 14 via the cable 33.

The wires 28, 30, 32 may be constituted by wires having a cross-sectional area of 0.14 mm², alternatively a cross-sectional area of 0.25 mm². In the presently preferred embodiment of the present invention, the cables are made from a material having a specific resistivity of 0.01725 ohm×mm²/m. Having a wire of the length of 30 m results in a total resistance of 7.4 ohm using a cable with a cross-sectional area of 0.14 mm² and 4.74 ohm using a wire having a cross-sectional area of 0.22 nm².

The circuitry shown in FIG. 2a also includes a central processor constituted by a CPU designated the reference numeral 56, which is connectable to an external data logger such as a computer through an RS-232 port.

Figure 2B:
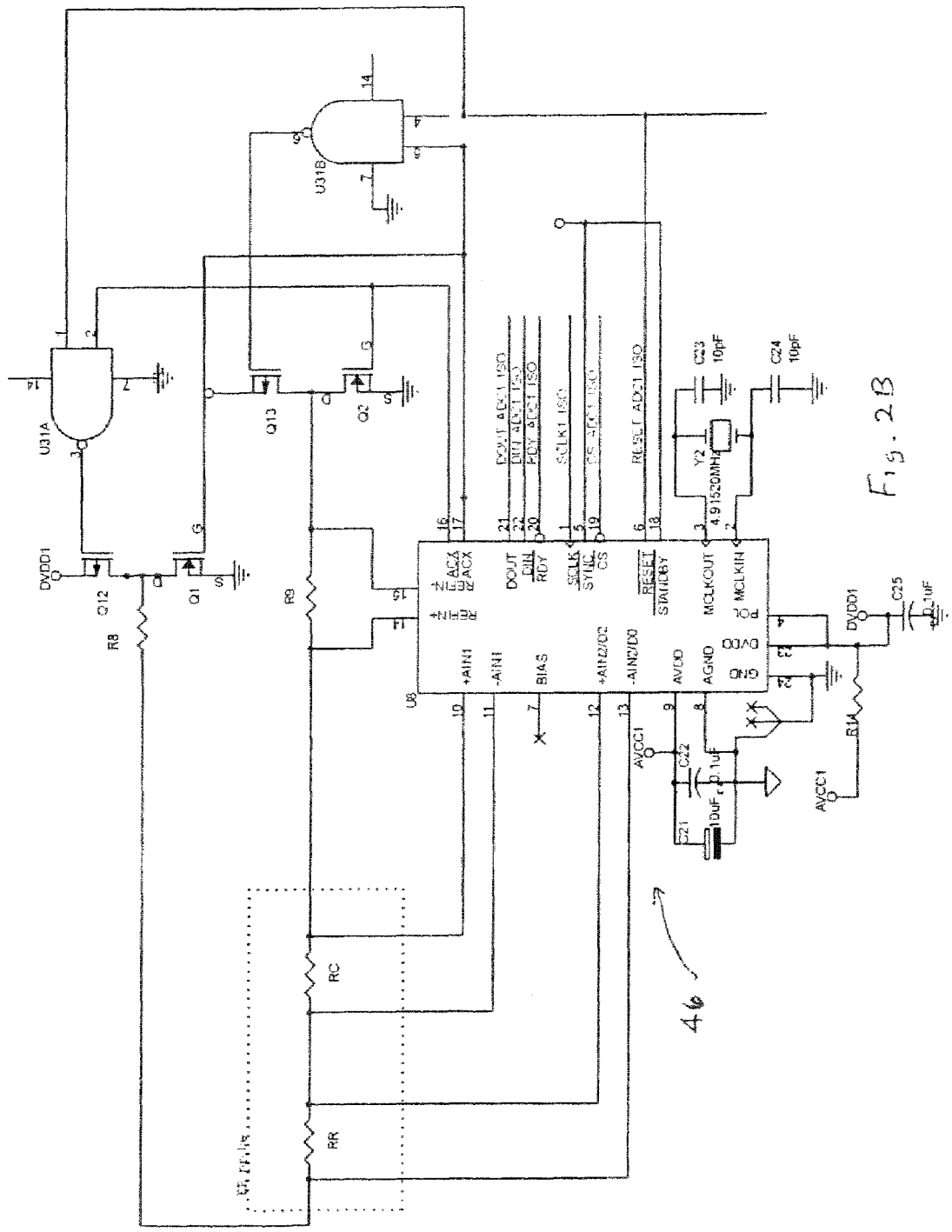
FIG. 2b is a schematic representation of the current excitation circuit in a measuring system according to the present invention.

In FIG. 2b, an electronic circuitry schematic is shown, illustrating in greater details the circuitry of the current excitation block 46, of FIG. 2a, and includes identification of the various components in mer us of type and value. No detailed description of the circuitry is given, as the circuitry is believed to be entirely self-explanatory.

In the presently preferred embodiment of the present invention, the measurement system 10 does not include a user interface such as a screen or display for outputting measurement results to a user. However, the system 10 includes, in the presently preferred embodiment of the present invention, a serial RS-232 port for reading out stored results from the memory of the system to an external data collecting source such as a computer.

Alternatively, the system may include other means for establishing communication between the measurement system 10 and an external data collecting source, such as a centralised surveillance system constituted by a server having a graphical user interface with the option of surveying and controlling several measuring posts in real time or near real time.

The communication between the measurement system 10 and the data collecting source may be constituted by a GSM module, wireless or wired LAN, satellite networks or a direct connection to a publicly switch telephone network, such as a digital subscriber line or the like.

The establishment of a centralised computer network may eliminate the need for sending out personnel to each of the measurement posts. However, establishing a large data network may be more expensive depending on the existing infrastructure.

The measurement system 10 may be pre-configured from the factory, but may preferably be configured for the individual need at the specific measuring post, wherein the system is installed. For easing the configuration of the system, a graphical user interface may be installed on an external computer such as a laptop operated by a technician installing the system at a specific measuring post.

As previously discussed, the connection between the external computer, e.g. laptop, may be constituted by wires or wireless connections, such as LAN, USB, fire wire (IEEE 1394), Bluetooth, RS-232 or similar connectors and connecting methods and communication protocols obvious to those skilled in the art.

Figure 3:
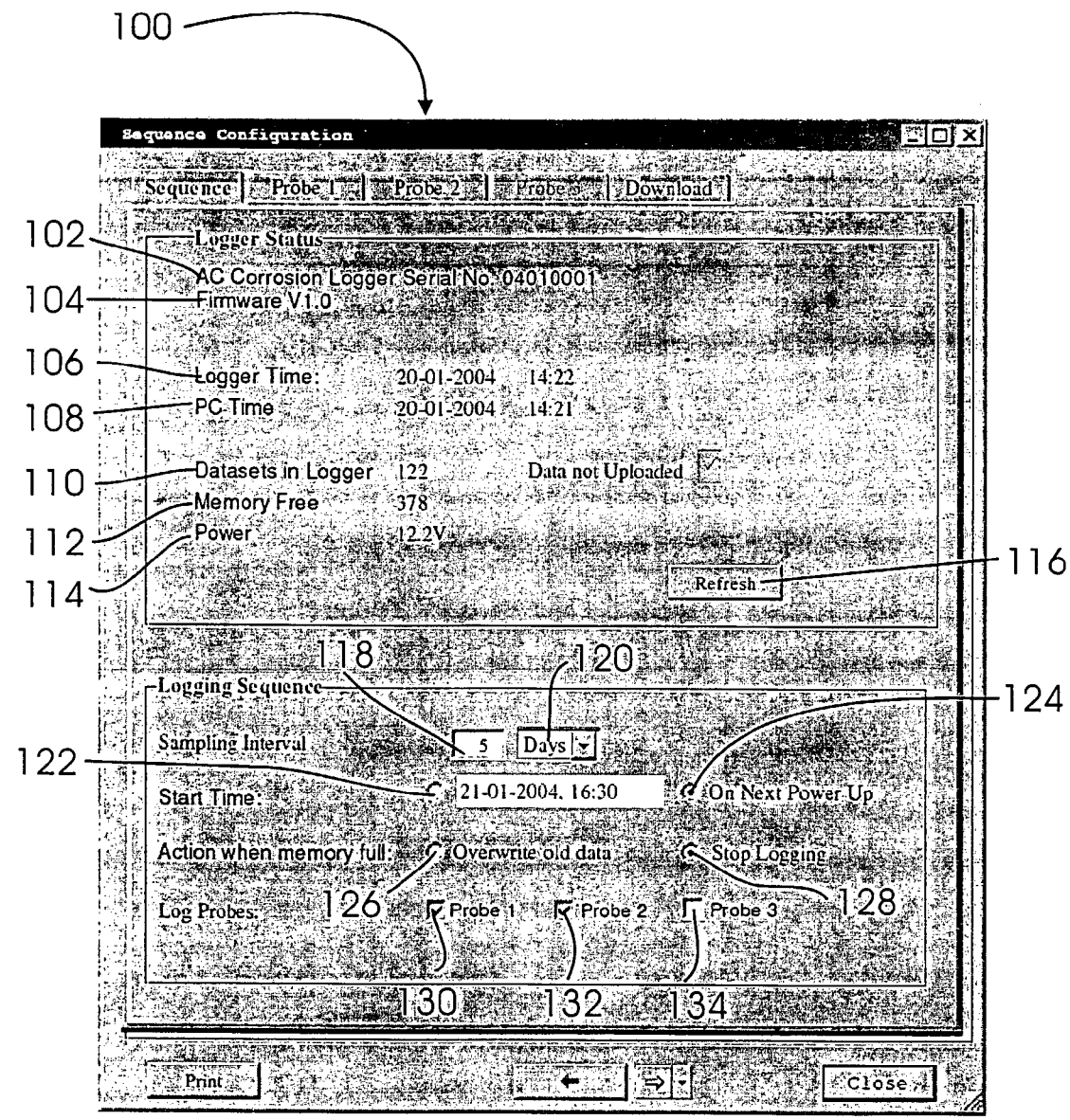
FIG. 3 illustrates a graphical user interface for displaying status of a measuring system according to the present invention.

FIG. 3 illustrates a graphical user interface for displacing the status of the data logging system of the measuring system 10. The logger status window 100 displays the serial number 102 for identifying the measuring system. Also displayed is a firmware version number 104 for the technician to ensure that the latest firmware version is installed on the system.

The technician also needs to ensure that the logger time, i.e. the time registered in the embedded system in the measuring device, is correct compared to the actual time. The technician may verify this by inspecting the logger time and the PC time as indicated at the numerals 106 and 108, respectively, of FIG. 3. The window also displays the number of data sets 110 recorded in the logger. The maximum number of data sets that may be recorded in the system at one time is limited by the amount of memory installed in the system. Presenting to the technician a number representing either the amount of free memory in kilobytes or number of data sets is displayed in the field 112 of the window 100.

As the measuring system may be powered by a battery source, an indication of the voltage available from the battery 114 is displayed. The technician may force the numbers displayed in the window 100 to be updated or refreshed by operating the button 116.

The technician operating the system may define how often the measuring system 10 should sample the probes 20, 22, 24 by setting a number in the box 118 corresponding to either a number of minutes, hours, days or weeks or months. The period being selected from a drop down box 120. The technician may further choose the time when the measuring system 10 should conduct the first sampling by choosing either of the radio buttons 122 or 124.

As the system has a limited amount of memory, the technician may choose to override old data or stop logging new data when the memory has been filled with data sets. The choice may be constituted by choosing a corresponding radio button 126 or 128. In the presently preferred embodiment of the present invention, the measuring system 10 comprises 3 probes, i.e. 3 connectors for receiving signals from at least 3 probes, and the technician has an option of choosing which of the 3 connectors/probes to sample data from. The choice may be made by checking a corresponding check box 130, 132 or 134.

Figure 4:
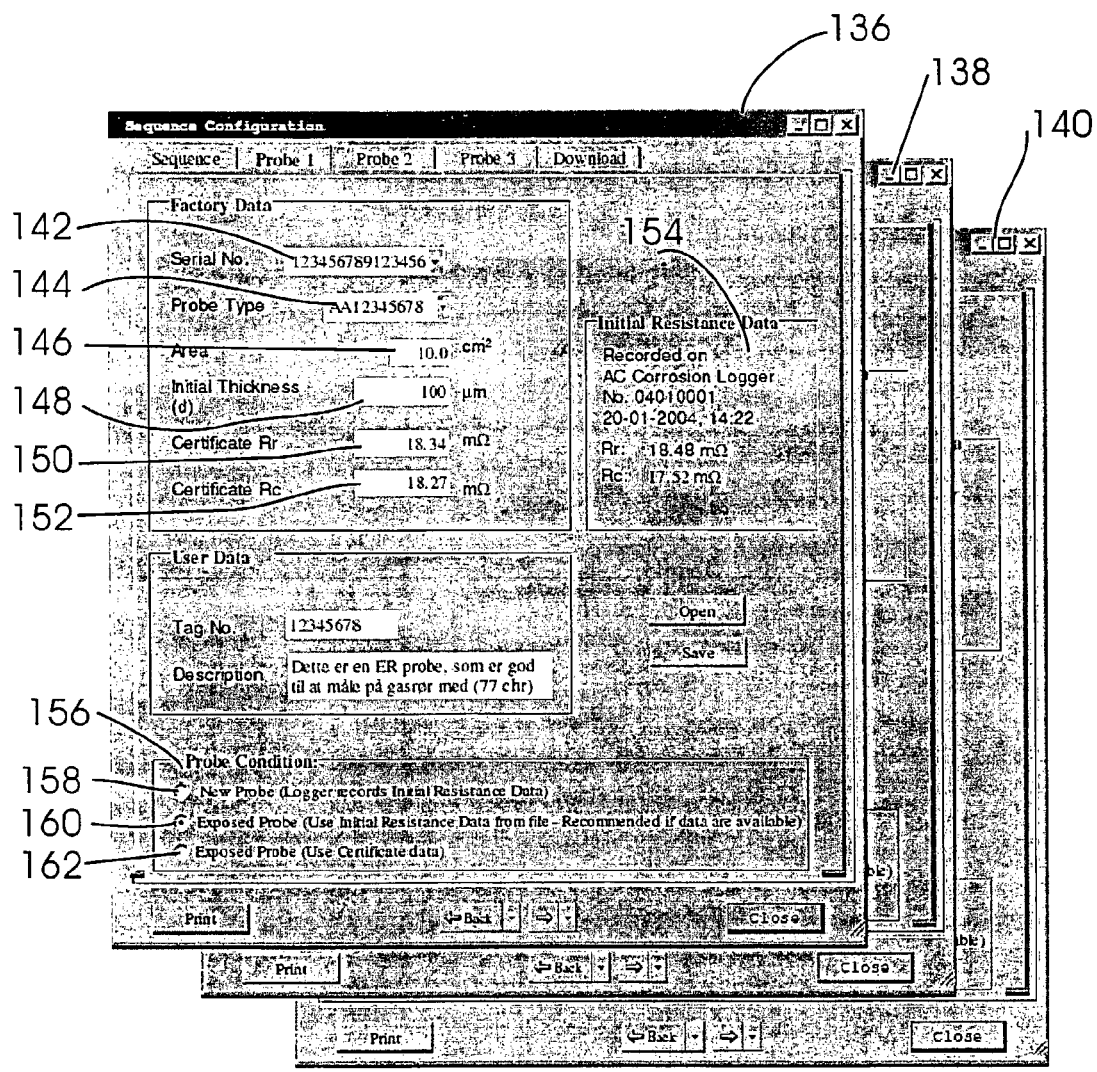
FIG. 4 illustrates a graphical user interfaces for probe configuration.

Each of the probes selected or activated by clicking either of the check boxes 130. 132, 134 may be set up in a corresponding set-up window 136, 138, 140, illustrated in FIG. 4. Each of the windows 136, 138, 140 comprises a probe serial number 142 indication and a probe type indication 144. The probe type 144 may determine the initial data to be filled into the boxes 146, 148, 150, 152 presenting respectively area, initial thickness, certificate Rr and certificate Rc. Each of the set-up windows 136, 138, 140 further comprises an initial resistance data section 154 comprising data collected from each of the probes at the initiation of the system 10.

During configuration of the system, the user/technician may choose in which condition the probes are placed and on which conditions the system should conduct the calculations and determine the state of the pipe. As indicated in the box 156, the probe may be a new probe 158 possibly placed above ground and the initial resistance data may be recorded. Alternatively, the probe may be exposed to the environment and the radio button 160 should be selected. The program then uses the initial resistance data collected when the system was first configured. If no initial resistance data is available, the radio button 162 may be chosen, and the program then utilizes the factory data available from the prototype indication.

As the technician has configured the system using the graphical user interface of FIG. 3 and FIG. 4, the set-up may be downloaded to the system 10.

Figure 5:
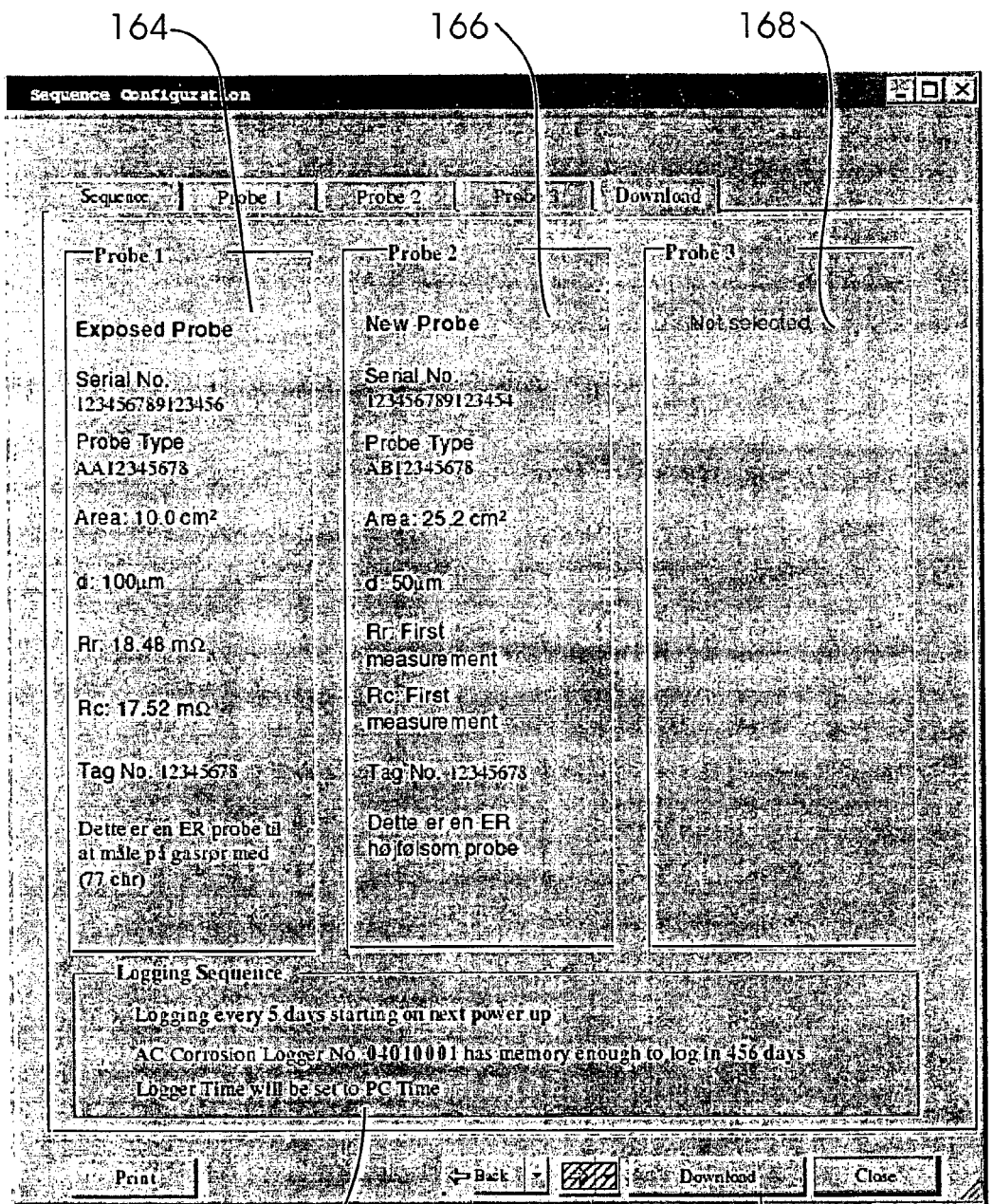
FIG. 5 illustrates a graphical user interface including a summary of the set-up for each of the probes.

In FIG. 5, a summary of the set-up is displayed for each of the probes in the boxes 164, 166, 168. As illustrated in box 168, it is indicated to the technician that no probe has been selected. In the box 170, a summary of the frequency of the logging is displayed, also an estimation of how long the system is able to log information before the memory is full is displayed.

Figure 6:
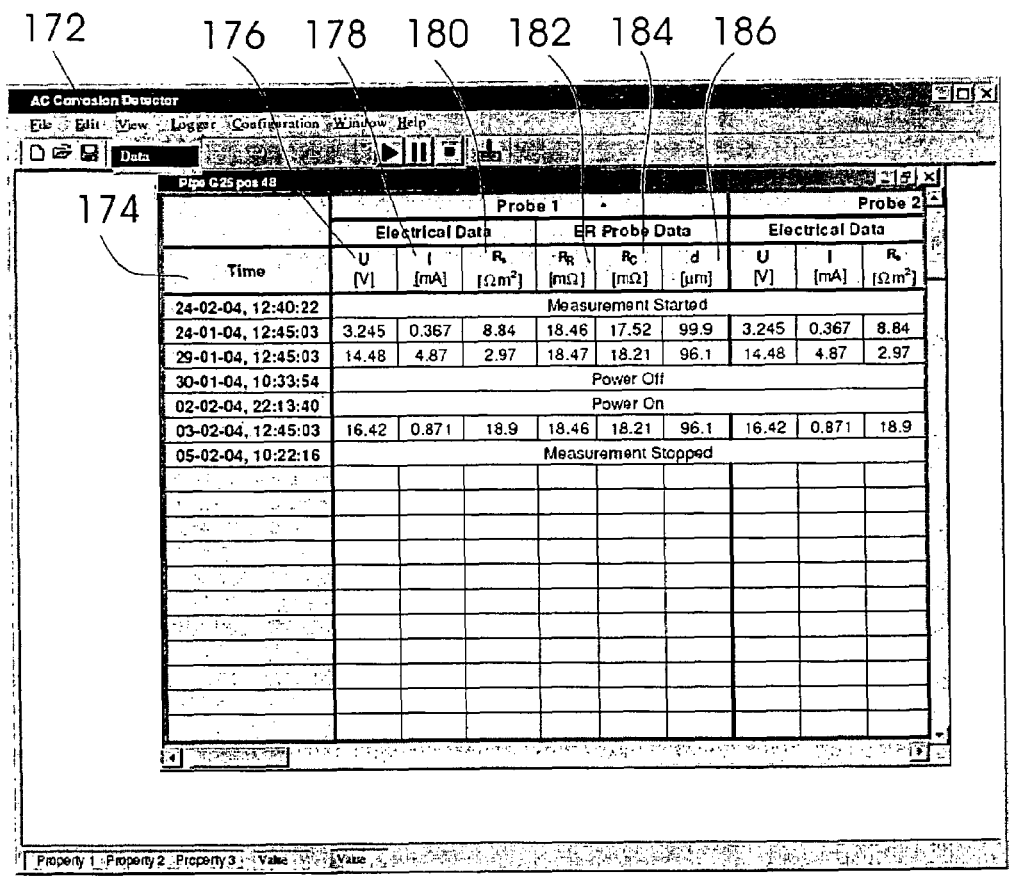
FIG. 6 illustrates a graphical user interface displaying a summary of measured and calculated data.

FIG. 6 illustrates a window 172 displaying data collected from a number of probes showing the time and date in a column 174 indicating when the event occurred.

Also displayed are columns comprising the voltage 176, current 178, spread resistance 180, resistance of the two parts of the electrical resistance probe named Rr 182, Rc 184 and the remaining element thickness D 186.

The thickness of the probe is determined according to the following equation:

$$d = \left(\frac{R_C(t_0)}{R_R(t_0)} \cdot \frac{R_R(t)}{R_C(t)}\right) \cdot 100$$

The embedded software in the system 10 controls the data logging and the power control of the system as well as sampling from each of the channels each representing a probe. In the presently preferred embodiment of the present invention, the user software is implemented on a windows platform and is used for setting up the data logger by setting the sampling interval and the clock. The user software uploads data from the data logger and calculates the element thickness, i.e. the decay of the probe. The user software also exports the uploaded data into a spread sheet compatible format, so that the data may be investigated or processed in such a spreadsheet.

The user software may include calibration software for downloading embedded software into the data logger and run specific tests and calibration routines and subsequently printing out or delivering a calibration certificate.

The user software may further include test software for viewing and configuring registers in the data logger for test purposes and reading out the raw and/or calculated data contained in the data logger. It is obvious to a technician skilled in the art that the calibration and test software may be supplied in one, two or three separate software packages with different user access rights if this may be more convenient or safe.

When powered up, the datalogger (ESW) will run with the saved settings.

On power up the ESW wakes up and reads settings. If a new probe is installed no values for $R_R(t_0)$ and $R_C(t_0)$ exist, and they first have to be measured and saved. They are not used in the logger, but will be used later, when data are uploaded for thickness calculations.

If $R_R(t_0)$ and $R_C(t_0)$ already exist in the setting, they will be saved with this.

On the user specified intervals the ESW wakes up by an interrupt from the Real Time Clock, performs a measurement on each of the user specified channels and measures Spread Resistance parameters ($V_{open}$ and $I_{closed}$).

For each measurement the following data are stored:
Time stamp (t)
$V_{open}$ (1 to 3) (AC voltage between pipe and probe)
$I_{closed}$ (1 to 3)
$R_R(t)$ (ch. 1 to 3)
$R_C(t)$ (ch. 1 to 3)

All data are saved in Non Volatile memory and ESW is returning to sleep mode. In case of power off ESW will stop logging as long as the power is off, but the logging will continue when it is reestablished.

The logger is connected to a PC and powered up. UPSW is started and used to set up the datalogger.

The user can enter data for the each probe:

| | Datatype | Range | default |
|---|---|---|---|
| Channel no. (1-3) | Flag in Sequence menu | 1-3 | |
| Probe type name (16 Characters) | Ascii | | blank |
| Initial $R_R(t_0)$ $R_C(t_0)$ (from certificate) | Num | 1.00-640.00 | 0 |

-continued

| | Datatype | Range | default |
|---|---|---|---|
| Initial thickness $d_0$ (μm) | Num | 1-1000 | 100 |
| Surface area A (cm$^2$) | Num | 0.1- | 10 |
| Probe serial no. (10 characters) | Ascii/Num | AA00000000 ZZ99999999 | |
| Probe tag. no. (8 characters) | Ascii | | blank |
| Probe text (80 characters) | Ascii | | blank |

The probe data also includes

| | Datatype | Range | default |
|---|---|---|---|
| Initial $R_R(t_0)$ $R_C(t_0)$ (measured) (mΩ) | Num | 1.00-640.00 | 20.00 |
| Measurement data | See paragraph on data representation | | |
| Serial no. of the logger used | Ascii/Num | AA00000000 ZZ99999999 | blank |
| Record Date | DD-MM-YYYY, HH:MM | | -- -- ---- --:-- |

Each probe channel is set up with the parameters
Log this probe (Yes or No)
New probe (Yes or No).
    If Yes, the no data for initial $R_R(t_0)$ and $R_C(t_0)$ are downloaded.
    If No the user can choose between
        $R_R(t_0)$ $R_C(t_0)$ are copied from certificate to measured $R_R(t_0)$ $R_C(t_0)$
        Enter new initial $R_R(t_0)$ and $R_C(t_0)$
Measurement Settings (all probes)
Action on overflow (Overwrite old data or stop sampling)
Start time (On next power up or specific Time)
Sampling interval (1 hour to 1 month)

When set up is finished, the user is given the total logging period, until memory will be full.

The Real Time Clock in the datalogger is synchronized with the PC clock when the sequence is downloaded to the logger.

Before disconnecting the datalogger from PC a "Measurement Check" can be performed to ensure that the logger is running correctly. This measurement is performed as fast as possible and is not saved as a result in the logging series.

The datalogger can now be powered off and installed on location.

The probe data are saved in a file identified by the probe serial number (probe file).

ESW can be waked up by connecting a PC to the RS232 interface. The data can be uploaded to the UPSW.

In normal upload, only one datalogging series can be uploaded.

Data can uploaded while the logging sequence is still running or in "pause" mode, but data in logger will still be labeled as "not uploaded", as soon as 1 new measurement has been performed.

On upload from a stopped logger, data will be labeled as "uploaded". Same data can be uploaded again until a new sequence is started.

A "Status" request gives the condition of the datalogger and doesn't affect the logging.

Data representation.

UPSW presents the data tabulated (and graphical).

From the raw values, that are uploaded UPSW calculates thickness (d) and Spread Resistance ($R_s$) for each probe.

d is the remaining element thickness at time t:

$$d(t) = \left(\frac{R_C(t_0)}{R_R(t_0)} \cdot \frac{R_R(t)}{R_C(t)}\right) \cdot d_0 \, [\mu m]$$

Ranges:

| | |
|---|---|
| $R_C$ & $R_R$: | 0-640 m$\Omega$ |
| d: | 1-1000 µm or disconnected |

Resolution

| | |
|---|---|
| $R_C$ & $R_R$: | 0.01 m$\Omega$ |
| d: | 0.1 µm |

When the pipe has an induced AC-voltage, the resistance between the pipe and each probe ($R_S$) can be calculated:

$$R_S = \frac{U_{open}[V]}{I_{closed}[A]} \cdot A[cm^2] \cdot \frac{1}{10.000}\left[\frac{m^2}{cm^2}\right] [\Omega \cdot m^2]$$

Ranges:
$U_{open}$: 1V-180V (RMS)
$I_{closed}$: 3 µA-600 mA
A: 0.1-50 cm$^2$ (Entered value)
$R_s$: 0.0003 $\Omega \cdot m^2$ / 1500 $\Omega \cdot m^2$ (R=30$\Omega$-300 k$\Omega$)
Resolution:
$U_{open}$: 1 mV$_{RMS}$
$I_{closed}$: 1 µA
A: 0.1 cm$^2$
$R_S$: Logarithmic with 3 significant numbers (dependent on the levels of $U_{open}$ and $I_{closed}$ & A).

Logging interval: Data are as default measured and logged once every week. Interval be set from 1 minute to 99 weeks.

Data storage: 1800 sets of data from 3 probes.

UPSW can export data in a tabulator-separated format for use in spreadsheets.

The Calibration software (CPSW) runs through a number of specific tests to verify the datalogger hardware and to certify the measurement performance. The following tasks are to be performed Load embedded software Test memory access Test RTC access Calibrate $R_R$ and $R_C$ for Channel 1 to 3. Wait for change of reference probe by operator.

Calibrate $R_s$ measurement for each channel.

If calibration results are within limits, save and print certificate.

All measurement data are logged in a file and can be retrieved for evaluation.

The graphical user interface, as illustrated in the FIGS. 3-5 may be implemented on any platform such as Windows, Unix, Linux or alternatively a proprietary operating system. Further alternatively, the graphical user interface may be implemented using HTML, dHTML, XML, CGI, JAVA or any other programming language.

Annex 1

1. DIN 50 929 part 3, Probability of corrosion of metallic materials when subjected to corrosion from the outside.
2. EN 12954, Cathodic protection of buried or immersed metallic structures—General principles and application for pipelines.
3. EN 13509, Cathodic protection measurements techniques.
4. prEN 50162, Protection against corrosion by stray current from direct current systems.
5. NACE Standard RP0169-96, Standard Recommended Practice: Control of External Corrosion on Underground or Submerged Metallic Piping Systems.
6. NACE Standard TM0497-97, Standard Test Method: Measurement Techniques Related to Criteria for Cathodic Protection on Underground or Submerged Metallic Piping Systems.
7. NACE Standard RP0177-2000, Standard Recommended Practice: Mitigation of Alternating Current and Lightning Effects on Metallic Structures and Corrosion Control Systems.
8. CeoCor Booklet, AC Corrosion on Cathodically Protected Pipelines—Guidelines for Risk Assessment and Mitigation Measures. (Proc 5$^{th}$ International Congress, Bruxelles 2000).
9. ASTM G 57-95A (Reaproved 2001): Standard Test Method for Field Measurement of Soil Resistivity Using the Wermer Four-Electrode Method.
10. International Patent Application, PCT/DK00/00689, publication number WO 01/42764, Method and Apparatus for Measuring Accumulated and Instant Rate of Material Loss or Material Gain,
11. General reference: Handbook of Cathodic Corrosion Protection, Theory and Practice of Electrochemical Protection Processes, 3$^{rd}$ edition, W. Von Baeckmann, W. Schwenk, and W. Prinz, Editors, Gulf Publishing (1997).

Annex 2

Requirement Specification

Corrosion Detector

1. Table of Contents
1. Table of Contents . . . 2
2. Revisions . . . 2
3. Corrosion Detector . . . 3
3.1. Functional requirements . . . 3
3.2. User interface . . . 3
3.3. Design requirements . . . 3
3.4. Specifications . . . 3
   3.4.1. Element thickness measurement . . . 3
   3.4.2. Spread Resistance . . . 4
   3.4.3. Data storage . . . 4
   3.4.4. Communication . . . 4
   3.4.5. Environment conditions . . . 4
3.5. Approvals . . . 5
2. Revisions
V010: 170603: Draft edition by Folke Galsgaard
V020: 190603: Reviewed by Lars Vendelbo Nielsen
V030: 120903: No. of probes changed to 3
Spread Resistance specifications changed.

3. Corrosion Detector

"Corrosion Detector" is a datalogger for measuring the environmental corrosivity.

3.1. Functional Requirements

Connection of 1 to 3 HSER (High Sensitive Electrical Resistance) probes.

Corrosion Detector is measuring the resistance of the two parts of a HSER probe named $R_R$ and $R_C$. A value of the remaining element thickness is calculated.

The potential between the pipe and the probes is equalized through the instrument. The spread resistances between the pipe and each probe ($R_S$) are regularly measured and logged.

3.2. User Interface

The Corrosion Detector works as a data logger. Data can be uploaded to a computer and saved as a tabulator separated file. Data analysis can be done in a spreadsheet (e.g. Excel).

The unit of the data is % of the initial value of $R_C$. The values are paired with a timestamp.

3.3. Design Requirements

The instrument is cased in a cabinet with the dimensions L×W×H=165×80×32 mm.

The 3 probe connectors are placed in one end of the case and the power inlet and communication connector in the other.

3.4. Specifications

3.4.1. Element Thickness Measurement

Remaining element thickness (d):
Range: 100% -20%
Resolution: 0.1% (1 ppt)
Accuracy: ±1% (±10 ppt)
Specified for a probe with $R_C(t_0)$=100 mΩ d is the remaining element thickness compared with the initial value.

$$d = \left( \frac{R_C(t_0)}{R_R(t_0)} \cdot \frac{R_R(t)}{R_C(t)} \cdot 100 \right) [\%]$$

Cable length: max. 30 m

3.4.2. Spread Resistance

When the pipe has an induced AC-voltage, the resistance between the pipe and each probe ($R_S$) is calculated and logged with every thickness measurement.

$R_S$ is calculated as $$R_S = \frac{U_{open}}{I_{short}}$$

Ranges:
$U_{open}$: 1V-180V (RMS)
$I_{short}$: 3 μA-600 mA
$R_S$: 300Ω-300 kΩ
Resolution:
$U_{open}$: 1 mV$_{RMS}$
$I_{short}$: 3 μA
$R_S$: Depending on the levels of $U_{open}$ and $I_{short}$
Examples: $U_{open}$=1 V, $I_{short}$=3 μA: $R_S$=333 kΩ, $\Delta R_S$=167 kΩ
$U_{open}$=1 V, $I_{short}$=6 μA: $R_S$=167 kΩ, $\Delta R_S$=111 kΩ
$U_{open}$=1 V, $I_{short}$=100 μA: $R_S$=10 kΩ, $\Delta R_S$=300Ω
$U_{open}$=1 V, $I_{short}$=1 mA: $R_S$=1 kΩ, $\Delta R_S$=3Ω
$U_{open}$=1 V, $I_{short}$=3.3 mA: $R_S$=300Ω, $\Delta R_S$=2Ω
$U_{open}$=20 V, $I_{short}$=67 μA: $R_S$=300 kΩ, $\Delta R_S$=15 kΩ
$U_{open}$=20 V, $I_{short}$=67 mA: $R_S$=300 Ω, $\Delta R_S$=15 mΩ

3.4.3. Data Storage

Update rate: Data are measured and logged once every week.

Data storage: 100 set of data from 3 probes giving approximately 2 years monitoring period.

Power Supply

The instrument is supplied from an external 12V$_{DC}$ supply, either from an adaptor or a lead battery.

| Power consumption: | 1 W (Average) |
|---|---|

3.4.4. Communication
RS232 interface.

3.4.5. Environment Conditions

| | |
|---|---|
| Operation temperature: | −30° C. to 50° C. (−86° F. to 122° F.) |
| Humidity: | 0 to 90% RH |
| Enclosure: | IP50 |

3.5. Approvals

The following directives and standards will be met:
EMC-Requirements
CE marking in accordance to EMC-directive 89/336/EEC
Following the standards
EN61326-1:1997 Electrical equipment for measuring, process control and laboratory use.
Amendment A1:1998 to EN 61326:1997
Amendment A2:2001 to EN 61326:1997
Electrical Safety
Low voltage directive 73/23/EØF
Following the standard
EN61010-1: Electrical safety
When powered from a 12V$_{DC}$ supply no requirements in EN61010 are required.

Annex 3

Software Requirement Specification

AC Corrosion Detector

1. Table of Contents
1. Table of Contents . . . 2
2. Revisions . . . 2
3. Introduction . . . 3
4. General Software Specifications . . . 3
5. Embedded Software (ESW) . . . 4
5.1. Datalogging . . . 4
   5.1.1. LED indication . . . 4
5.2. Data Upload . . . 5
5.3. Hardware description . . . 5
6. User PC software (UPSW) . . . 5
6.1. Setting up and starting the datalogger . . . 5
6.2. Data upload . . . 6
6.3. Data presentation . . . 7
   6.3.1. Probe element thickness . . . 7
   6.3.2. Spread Resistance . . . 7
   6.3.3. Data storage . . . 8
7. Calibration software PC software (CPSW) . . . 8
8. Test software (TPSW) . . . 8
2. Revisions
V010: 021203: Draft edition by Folke Galsgaard
V020: 031203: Reviewed by LVN
V030: 041203: Several changes V040: 091203: Changes after initial meeting with Ramtex
V100: 110104: Document release 3. Introduction "AC Corrosion Detector" (ACD) is a data logger for assessment of the corrosion risk along buried high-pressure gas transmission pipelines due to a combined effect of soil chemistry and electrical parameters (induced AC voltage—DC stray currents).

Connection of 1 to 3 ER (Electrical Resistance) probes.

ACD is measuring the resistance of the two parts of an ER probe named $R_R$ and $R_C$. A value of the remaining element thickness is calculated.

The potential between the pipe and the probes is equalized through the instrument. The spread resistances between the pipe and each probe ($R_S$) are regularly measured and logged.

4. General Software Specifications

The software for the AC Corrosion Detector consists of the following 4 parts[1].

[1] The 3 PC software parts could be part of the same "package" and separated with different user access rights, if this is the most convenient.

Embedded Software (ESW)
Control of the datalogging including power control and sampling from each channel using a downloaded setup.
Saving "raw" data in the logger memory
Upload of data via RS232
Synchronizing Real Time clock with PC.
User PC Software (UPSW)
Windows platform
Setting up the datalogger (sampling interval, clock)
Uploading data from datalogger and calculate element thickness (decay).
Exporting data in a spreadsheet compatible format.
Calibration Software PC Software (CPSW)
Windows platform
Download ESW software to datalogger
Run through a specific production test and calibration
Printout a calibration certificate.
Test Software (TPSW)
Windows platform
Viewing and setting registers in the datalogger for test purposes.
Readout of "raw" and calculated data.
Download the ESW software to datalogger 5. Embedded Software (ESW)

The embedded software (ESW) shall control the data logging functions, calculate the probe data and on command transmit data to the PC. The data logging functions includes power management of the data acquisition and the CPU.

5.1. Datalogging

When powered up, the datalogger (ESW) will run with the saved settings.

On power up the ESW wakes up and reads settings. If a new probe is installed no values for $R_R(t_0)$ and $R_C(t_0)$ exist, and they first have to be measured and saved. They are not used in the logger, but will be used later, when data are uploaded for thickness calculations.

If $R_R(t_0)$ and $R_C(t_0)$ already exist in the setting, they will be saved with this.

On the user specified intervals the ESW wakes up by an interrupt from the Real Time Clock, performs a measurement on each of the user specified channels and measures Spread Resistance parameters ($V_{open}$ and $1_{closed}$).

For each measurement the following data are stored:
Time stamp (t)
$V_{open}$ (1 to 3) (AC voltage between pipe and probe)
$1_{closed}$ (1 to 3)
$R_R(t)$ (ch. 1 to 3)
$R_C(t)$ (ch. 1 to 3)

All data are saved in Non Volatile memory and ESW is returning to sleep mode. In case of power off ESW will stop logging as long as the power is off, but the logging will continue when it is reestablished.

5.1.1. LED Indication

The LED indicator shall give information of the logger mode.

| Logger Mode | Frequency | On time | Duration |
| --- | --- | --- | --- |
| Power up and no logging sequence activated: | — | 5 s | 5 s |
| RS232 connection detected | — | 20 s | 20 s or communication started |
| Upload or download | 2 s | 1 s | On communication |
| Performing "Fast measurement" | 0.5 s | 100 ms | Until data is sent to PC |
| Start logging | 2 s | 500 ms | 2 min. then constant off. |

5.2. Data Upload

ESW can be waked up by connecting a PC to the RS232 interface. The data can be uploaded to the UPSW.

5.3. Hardware Description

The data logger hardware is built around the µProcessor Renesas H8S/2239.

Detailed description of the hardware is found in the document HYPERLINK..\Hardware\AC Corrosion Detector hardware description V100.doc 6. User PC Software (UPSW)

6.1. Setting Up and Starting the Datalogger

The logger is connected to a PC and powered up. UPSW is started and used to set up the datalogger.

The user can enter data for the each probe:

| | Datatype | Range | default |
| --- | --- | --- | --- |
| Channel no. (1-3) | Flag in Sequence menu | 1-3 | |
| Probe type name (16 Characters) | Ascii | | blank |
| Initial $R_R(t_0)$ $R_C(t_0)$ (from certificate) | Num | 1.00-640.00 | 0 |
| Initial thickness $d_0$ (µm) | Num | 1-1000 | 100 |
| Surface area A (cm$^2$) | Num | 0.1- | 10 |
| Probe serial no. (10 characters) | Ascii/Num | AA00000000 ZZ99999999 | |
| Probe tag. no. (8 characters) | Ascii | | blank |
| Probe text (80 characters) | Ascii | | blank |

The probe data also includes

|  | Datatype | Range | default |
|---|---|---|---|
| Initial $R_R(t_0)$ $R_C(t_0)$ (measured) (mΩ) | Num | 1.00-640.00 | 20.00 |
| Measurement data | | See 6.3 Data presentation | |
| Serial no. of the logger used | Ascii/Num | AA00000000 ZZ99999999 | blank |
| Record Date | DD-MM-YYYY, HH:MM | | -- -- ---- --:-- |

Each probe channel is set up with the parameters
Log this probe (Yes or No)
New probe (Yes or No).
   If Yes, the no data for initial Rhd $R(t_0)$ and $R_C(t_0)$ are downloaded.
   If No the user can choose between
     $R_R(t_0)$ $R_C(t_0)$ are copied from certificate to measured $R_R(t_0)$ $R_C(t_0)$
     Enter new initial $R_R(t_0)$ and $R_C(t_0)$
Measurement Settings (All Probes)
Action on overflow (Overwrite old data or stop sampling)
Start time (On next power up or specific Time)
Sampling interval (1 hour to 1 month)

When set up is finished, the user is given the total logging period, until memory will be full.

The Real Time Clock in the datalogger is synchronized with the PC clock when the sequence is downloaded to the logger.

Before disconnecting the datalogger from PC a "Measurement Check" can be performed to ensure that the logger is running correctly. This measurement is performed as fast as possible and is not saved as a result in the logging series.

The datalogger can now be powered off and installed on location.

The probe data are saved in a file identified by the probe serial number (probe file).

6.2. Data Upload

ESW can be waked up by connecting a PC to the RS232 interface. The data can be uploaded to the UPSW.

In normal upload, only one datalogging series can be uploaded.

Data can uploaded while the logging sequence is still running or in "pause" mode, but data in logger will still be labeled as "not uploaded", as soon as 1 new measurement has been performed.

On upload from a stopped logger, data will be labeled as "uploaded". Same data can be uploaded again until a new sequence is started.

A "Status" request gives the condition of the datalogger and doesn't affect the logging.

6.3. Data Presentation

UPSW presents the data tabulated (and graphical).

From the raw values, that are uploaded UPSW calculates thickness (d) and Spread Resistance ($R_s$) for each probe.

6.3.1. Probe Element Thickness d is the remaining element thickness $$d(t) = \left(\frac{R_C(t_0)}{R_R(t_0)} \cdot \frac{R_R(t)}{R_C(t)}\right) \cdot d_0 \, [\mu m]$$

Ranges:

| | |
|---|---|
| $R_C$ & $R_R$: | 0-640 mΩ |
| d: | 1-1000 μm or disconnected |

Resolution

| | |
|---|---|
| $R_C$ & $R_R$: | 0.01 mΩ |
| d: | 0.1 μm |

6.3.2. Spread Resistance

When the pipe has an induced AC-voltage, the resistance between the pipe and each probe ($R_S$) can be calculated:

$$R_S = \frac{U_{open}[V]}{I_{closed}[A]} \cdot A[cm^2] \cdot \frac{1}{10.000}\left[\frac{m^2}{cm^2}\right] [\Omega \cdot m^2]$$

Ranges:
$U_{open}$: 1V -180V (RMS)
$I_{closed}$: 3 μA-600 mA
A: 0.1-50 cm² (Entered value)
$R_S$: 0.0003 Ω·m²-1500 Ω·m² (R=30Ω-300 kΩ)
Resolution:
$U_{open}$: 1 mV$_{RMS}$
$I_{closed}$: 1 μA
A: 0.1 cm²
$R_S$: Logarithmic with 3 significant numbers (dependent on the levels of $U_{open}$ and $I_{closed}$ & A).

6.3.3. Data Storage

Logging interval: Data are as default measured and logged once every week. Interval be set from 1 minute to 99 weeks.

Data storage: 1800 sets[2] of data from 3 probes.

[2]TBD

UPSW can export data in a tabulator separated format for use in spreadsheets.

7. Calibration Software PC Software (CPSW)

The Calibration software (CPSW) runs through a number of specific tests to verify the datalogger hardware and to certify the measurement performance. The following tasks are to be performed
   Load embedded software
   Test memory access
   Test RTC access
   Calibrate $R_R$ and $R_C$ for Channel 1 to 3. Wait for change of reference probe by operator.
   Calibrate $R_s$ measurement for each channel.
   If calibration results are within limits, save and print certificate.

All measurement data are logged in a file and can be retrieved for evaluation.

8. Test Software (TPSW)

The test software shall run as the user software (UPSW) but with access to more data (raw data) and with access to setting up the some of the parameters in the datalogger.
   Set up parameters
   ADC (1-3) set up as
     Data Rate,
     Input Range,
     Delay time,
     TARE DAC,
     AC excitation,
     number of samples (1 to 2000)
   Perform Internal Zero scale Perform Internal Full Scale calibration
Perform External Full scale calibration
ADC (0)
  Data Rate
  Input Range
  number of samples (1 to 5000)
Force power on channel 0-3
Measurements
Raw Data
$V_{open}$
  ADC0 (Channel 1 to 3)
$I_{closed}$
  ADC0 channel 0
$R_R(t)$
  ADC 1 to 3
$R_C(t)$
  ADC 1 to 3
The logger can be set to
Single step measurement sequence.
Continuously measuring as fast as possible Annex 4

AC Corrosion Detector

Hardware Description

1. Contents
1. Contents . . . 2
2. Revisions . . . 2
3. Introduction . . . 3
4. CPU . . . 3
4.1. Memory . . . 3
4.2. Jumper Settings . . . 3
4.3. Communication . . . 4
4.4. I/O Ports . . . 4
5. RTC . . . 9
6. AD-Converters . . . 10
6.1. Setting ADC1 to ADC3 (AD7730) . . . 10
6.2. Measure ADC 1-ADC 3 . . . 11
6.3. Setting ADC0 (AD7734) . . . 11
6.4. Measure ADC0 . . . 12
  6.4.1. Channel 0 . . . 12
  6.4.2. Channel 1-3 . . . 12
7. Power Supplies . . . 12
7.1. Control of Supplies . . . 13
7.2. Potentials . . . 14
7.3. Power Monitor . . . 14
8. Measurement Sequence . . . 15
9. Related Documents . . . 18
2. Revisions
090104: V100: First Issue Made by Folke Galsgaard
290104: V110: Corn_Power on CPU Port 72.
Memory allocation updated
3. Introduction
This document describes the hardware in the AC Corrosion Detector and how it is accessed by the embedded software.

4. CPU
The CPU is a Renesas H8S/2239
Operating Frequency $\phi$=8 MHz
4.1. Memory
384 kB on chip Flash memory
32 kB on chip Static RAM
64 kB E$^2$PROM (M24512)
H8S/2239 normally runs in single chip operating mode (7) using on chip memory, but for emulation and debugging on chip ROM can be disabled and instead 512 kB external memory addressed by setting operating mode 5.
Probe Setup and calibration data: 124 Bytes×3 probes=372 Bytes

| Measurements: | | |
|---|---|---|
| | $R_C$: 0.0 to 600.0 m$\Omega$ | 2 Bytes |
| | $R_R$: 0.0 to 600.0 m$\Omega$ | 2 Bytes |
| | $I_{closed}$: 0.000-700.000 mA$_{RMS}$ | 4 Bytes |
| | $U_{open}$: 0.00-195.00 V$_{RMS}$: | 4 Bytes |
| | | 12 Bytes |
| Memory per measurement 1 probe: | Time stamp: | 2 Bytes |
| | Power measurement | 2 Bytes |
| | | 1 Byte |
| | | 5 Bytes |
| Common data | | |

1500 measurements memory space=(12×3+5) 1500=61500 Bytes
Extra memory space: 65536−372−61500=3664 Bytes
4.2. Jumper Settings

TABLE 1

| JP3 and JP4 settings | | |
|---|---|---|
| | 0 (Jumper) | 1 (No Jumper) |
| JP1, Download/debug (FWE) | See. H8S2239 manual section 19 | Flash Protected |
| JP2, Reset | Reset (rising edge) | Release |
| JP3 (MD2) Boot mode | JP4 (MD1) Ext. PROM | |
| 0 | 0 | — |
| 0 | 1 | Boot mode |
| 1 | 0 | Mode 5, On chip ROM disabled |
| 1 | 1 | Mode 7, Single chip mode |

4.3. Communication
The E$^2$PROM is addressed on the I$^2$C interface and has the slave address 1010111 followed by the direction bit (R/W_).
CPU communicates with the ADCs with SPI interface. The required transfer rates are:
ADC0 samples with 1008 Hz giving a bitrate of 24.2 kb/s.
ADC1-3 samples with up to 400 Hz giving of bitrate of 9.6 kb/s
The interface is a "Clocked Synchronous Mode". The Bit Rate Register (BBR) is set to 50 kb/s. For $\phi$=8 MHz: n=0 og N=39.
4.4. I/O Ports

TABLE 2

| Pins og Port settings on H8S/2239 | | | | |
|---|---|---|---|---|
| Pin | CPU port | I/O | Name | Function/Setting |
| 1 | PE5/D5 | O PE5DDR = 1 PE5DR = 1 | Relay2_open | Opens Relay2 (H) |

TABLE 2-continued

Pins og Port settings on H8S/2239

| Pin | CPU port | I/O | Name | Function/Setting |
|---|---|---|---|---|
| 2 | PE/D6 | O<br>PE6DDR = 1<br>PE6DR = 1 | Relay3_open | Opens Relay3 (H) |
| 3 | PE7/D7 | O<br>PE7DDR = 1<br>PE7DR = 1 | RTS | |
| 4 | PD0/D8 | Data | D0 | |
| 5 | PD1/D9 | Data | D1 | |
| 6 | PD2/D10 | Data | D2 | |
| 7 | PD3/D11 | Data | D3 | |
| 8 | PD4/D12 | Data | D4 | |
| 9 | PD5/D13 | Data | D5 | |
| 10 | PD6/D14 | Data | D6 | |
| 11 | PD7/D15 | Data | D7 | |
| 12 | — | | CVCC | |
| 13 | PC0/A0 | Address | A0 | |
| 14 | — | | VSS | |
| 15 | PC1/A1 | Address | A1 | |
| 16 | PC2/A2 | Address | A2 | |
| 17 | PC3/A3 | Address | A3 | |
| 18 | PC4/A4 | Address | A4 | |
| 19 | PC5/A5 | Address | A5 | |
| 20 | PC6/A6 | Address | A6 | |
| 21 | PC7/A7 | Address | A7 | |
| 22 | PB0/A8/TIOCA3 | Address | A8 | |
| 23 | PB1/A9/TIOCB3 | Address | A9 | |
| 24 | PB2/A10/TIOCC3 | Address | A10 | |
| 25 | PB3/A11/TIOCD3 | Address | A11 | |
| 26 | PB4/A12/TIOCA4 | Address | A12 | |
| 27 | PB5/A13/TIOCB4 | Address | A13 | |
| 28 | PB6/A14/TIOCA5 | Address | A14 | |
| 29 | PB7/A15/TIOCB5 | Address | A15 | |
| 30 | PA0/A16 | Address | A16 | |
| 31 | PA1/A17/TxD2 | Address | A17 | |
| 32 | PA2/A18/RxD2 | Address | A18 | |
| 33 | PA3/A19/SCK2 | Open Drain<br>PA3DDR = 1<br>PA3ODR = 1<br>CKE0 = 0<br>CKE1 = 0<br>C/A = 0 | Power3_EN | Enables Power for ADC3 |
| 34 | P10/TIOCA0/DACK0/A20 | Out<br>P10DDR = 1<br>SAE0 = 0 | RESET_ADC | Resets selected ADC |
| 35 | P11/TIOCB0/DACK1/A21 | In<br>P11DDR = 0<br>SAE1 = 0 | | |
| 36 | P12/TIOCC0/TCLKA/A22 | Out<br>P12DDR = 1 | | — |
| 37 | P13/TIOCD0/TCLKB/A23 | Out<br>P13DDR = 1 | | — |
| 38 | P14/TIOCA1/IRQ0_ | Out<br>P14DDR = 1<br>In<br>P14DDR = 0 | SDA | SDA (I$^2$C) |
| 39 | P15/TIOCB1/TCLKC | Out<br>P15DDR = 1 | SCL | SCL (I$^2$C) |
| 40 | P16/TIOCA2/T\R\Q\1\ | Out<br>P16DDR = 1 | EE_WC_ | E$^2$PROM write Operations disabled (H) |
| 41 | P17/TIOCB2/TCLKD | Out<br>P17DDR = 1 | | — |
| 42 | — | | AVSS | — |
| 43 | P97/DA1 | In | | |
| 44 | P96/DA0 | In | | |
| 45 | P47/AN7 | In | | VCC |
| 46 | P46/AN6 | In | | |
| 47 | P45/AN5 | In | Input_Voltage | Input on ADC<br>$0.154 \times V_{input}$<br>(FS = 21.4 V) |
| 48 | P44/AN4 | In | | |
| 49 | P43/AN3 | In | | |
| 50 | P42/AN2 | In | | |
| 51 | P41/AN1 | In | | |
| 52 | P40/AN0 | In | | |

TABLE 2-continued

Pins og Port settings on H8S/2239

| Pin | CPU port | I/O | Name | Function/Setting |
|---|---|---|---|---|
| 53 | — | — | Vref. | Reference: 3.3 V |
| 54 | — | — | AVCC | |
| 55 | MD0 | I | 1 | Operating mode = 7: |
| 56 | MD1 | I | 1 (0 for mode 5) | Single chip mode. |
| 67 | MD2 | I | 1 (0 for boot mode) | |
| 57 | — | | | 32.768 KHz X-tal |
| 58 | — | | | 32.768 KHz X-tal |
| 59 | — | | RESET_ | |
| 60 | — | — | NMI_ | |
| 61 | — | — | STBY_ | |
| 62 | — | — | VCC_ | |
| 63 | — | — | XTAL_ | |
| 64 | — | — | VSS_ | |
| 65 | — | — | EXTAL_ | |
| 66 | — | — | FWE_ | |
| 68 | PF7/φ | Out PF7DDR = 1 | PF7 | NC |
| 69 | AS_/PF6 | Out Mode7: PF6DDR = 1 | AS_ | NC |
| 70 | PF5/RD_ | Out Mode7: PF5DDR = 1 | RD- | Read |
| 71 | PF4/HWR_ | Out Mode7: PF4DDR = 1 | HWR- | HighWrite |
| 72 | PF3/L\W\RVADTRG/IRQ3- | In 8bit bus mode PF3DDR = 0 IRQ3SCB = 10 | PGOOD | Interrupt when power stable (rising edge) |
| 73 | PF2/WAIT_ | Out PF2DDR = 1 Mode5: WAITE = 0 | | NC |
| 74 | PF1/BACK_/BUZZ | Out BUZZE = 0 PF1DDR = 1 Mode5: BRLE = 0 | | NC |
| 75 | PF0/BREQ_\IRQ2_ | In PF0DDR = 0 IRQ2SCB = 01 | RDY_ADC | Data from ADC ready |
| 76 | P30/TxD0 | Out TE = 1 P30ODR = 0 (push-pull) | RS232_TxD | |
| 77 | P31/RxD0 | In RE = 1 P31ODR = 0 (push-pull) | RS232_RxD | |
| 78 | P32/SCK0/SDA1/IRQ4 | I | DTR | |
| 79 | P33/TxD1/SCL1 | TE = 0 ICE = 0 P33DDR = 1 P33ODR = 1 (Open Drain) | Power0_EN | Enables Power for ADC0 |
| 80 | P34/RxD1/SDA0 | RE = 0 ICE = 0 P34DDR = 1 P34ODR = 1 (Open Drain) | Power1_EN | Enables Power for ADC1 |
| 81 | P35/SCK1/SL0/IRQ5_ | ICE = 0 CKE1 = 0 P33DDR = 1 P33ODR = 1 (Open Drain) | Power2_EN | Enables Power for ADC2 |
| 82 | P36 | P36DDR = 1 P36ODR = 1 (Open | Power_Shut_Down | Disables VCC3V and VCC5V (L). Starts |

TABLE 2-continued

Pins og Port settings on H8S/2239

| Pin | CPU port | I/O | Name | Function/Setting |
|---|---|---|---|---|
| | | Drain) | | automatically at power up. |
| 83 | P77/TxD3 | TE = 1 | DIN_ADC | SPI data to ADC |
| 84 | P76/RxD3 | RE = 1 | DOUT_DATA | SPI data from ADC |
| 85 | P75/TMO3/SCK3 | CKE1 = 0<br>C/A_ = 1 | SCLK | SPI CLK |
| 86 | P74/TMO2/MRES_ | Out<br>OS3 til<br>OS0 = 0<br>P74DDR = 1 | Front_LED | |
| 87 | P73/TMO1/TEND1_/CS7_ | Out<br>TEE1 = 0<br>OS3 til<br>OS0 = 0<br>P73DDR = 1 | Measure_DC_IN | Control measure of DC Input Voltage.<br>0 when not measuring. |
| 88 | P72/TMO0/TEND0_/CS6_ | Out<br>TEE0 = 0<br>OS3 til<br>OS0 = 0<br>P72DDR = 1 | Com_Power | Sets Power on RS232 Communication (L) |
| 89 | P71/MRI23/TMCI23/DREQ1_/CS5_ | Out<br>P71DDR = 1 | | |
| 90 | P70/MRI01/TMCI01/DREQ0_/CS4_ | Out<br>P70DDR = 1 | | |
| 91 | PG0/IRQ6_ | In<br>PG0DDR = 0 | RTC_interrupt | When this pin is used as an external interrupt pin, do not specify other functions. |
| 92 | PG1/C\S\3IRQ7_ | PG1DDR = 1 | | |
| 93 | PG2/CS2_ | PG2DDR = 1 | | |
| 94 | PG3/CS1_ | PG3DDR = 1 | | |
| 95 | PG4/CS0- | Out<br>PG4DDR = 1 | CS0- | Chip Select Extern Flash |
| 96 | PE0/D0 | O<br>PE0DDR = 1<br>PE0DR = 1 | CS_ADC0 | Enables ADC0 and isolator (L) |
| 97 | PE1/D1 | O<br>PE1DDR = 1<br>PE1DR = 1 | CS_ADC1 | Enables ADC1 and isolator (L) |
| 98 | PE2/D2 | O<br>PE2DDR = 1<br>PE2DR = 1 | CS_ADC2 | Enables ADC2 and isolator (L) |
| 99 | PE3/D3 | O<br>PE3DDR = 1<br>PE3DR = 1 | CS_ADC3 | Enables ADC3 and isolator (L) |
| 100 | PE4/D4 | O<br>PE4DDR = 1<br>PE4DR = 1 | Relay1_open | Opens Relay1 (H) |

5. RTC

The Real Time Clock is used for making time stamps on the measurements. A Maxim/Dallas DS1339 is used.

The RTC is addressed on the I²C interface and has the slave address 1101000 followed by the direction bit (R/W_).

DS1339 can switch between the power supply and the battery back up. It can also trickle charge the battery, if a rechargeable battery is used, however in this case a Li battery is used, and this must not be charged.

The tricklecharge select (TCS) bits (bits 4-7) control the selection of the trickle charger. In order to prevent accidental enabling, only a pattern on 1010 enables the trickle charger. All other patterns disable the trickle charger. The trickle charger is disabled when power is first applied.

FIG. 1. Trickle charge register (10h) bit values

| BIT 7<br>TCS3 | BIT 6<br>TCS2 | BIT 5<br>TCS1 | BIT 4<br>TCS0 | BIT 3<br>DS1 | BIT 2<br>DS0 | BIT 1<br>ROUT1 | BIT 0<br>ROUT0 | FUNCTION |
|---|---|---|---|---|---|---|---|---|
| X | X | X | X | 0 | 0 | X | X | Disabled |
| X | X | X | X | 1 | 1 | X | X | Disabled |
| X | X | X | X | X | X | 0 | 0 | Disabled |
| 1 | 0 | 1 | 0 | 0 | 1 | 0 | 1 | No diode, 250_resistor |

-continued

FIG. 1. Trickle charge register (10h) bit values

| BIT 7 TCS3 | BIT 6 TCS2 | BIT 5 TCS1 | BIT 4 TCS0 | BIT 3 DS1 | BIT 2 DS0 | BIT 1 ROUT1 | BIT 0 ROUT0 | FUNCTION |
|---|---|---|---|---|---|---|---|---|
| 1 | 0 | 1 | 0 | 1 | 0 | 0 | 1 | One diode, 250_resistor |
| 1 | 0 | 1 | 0 | 0 | 1 | 1 | 0 | No diode, 2k_resistor |
| 1 | 0 | 1 | 0 | 1 | 0 | 1 | 0 | One diode, 2k_resistor |
| 1 | 0 | 1 | 0 | 0 | 1 | 1 | 1 | No diode, 4k_resistor |
| 1 | 0 | 1 | 0 | 1 | 0 | 1 | 1 | One diode, 4k_resistor |

Control Register (0Eh)

TABLE 3

Control Register

| | Bit 7 | Bit 6 | Bit 5 | Bit 4 | Bit 3 | Bit 2 | Bit 1 | Bit 0 |
|---|---|---|---|---|---|---|---|---|
| Name | EOSC | 0 | BBSQI | RS2 | RS1 | INTCN | A2IE | A1IE |
| Setting | 0 | 0 | 1 | ∅ | ∅ | | 1 | 1 |

EOSC

To keep the power consumption from the battery down, the Oscillator is not running until the EOSC register is set to logic 0.

BBSQI

This bit must be set to a logic 1 to enable the interrupt output when Vcc is absent and the DS1339 is being powered by the $V_{BACKUP}$ pin.

INTCN (Interrupt Control)—This bit controls the relationship between the two alarms and the interrupt output pins. The INTCN bit must be set to logic 1, so that a match between the timekeeping registers and the Alarm 1 or Alarm 2 registers will activate the SQW/INT pin (provided that the alarms are enabled).

A1IE (Alarm 1 Interrupt Enable)—When set to logic 1, this bit permits the A1F bit in the status register to assert SQW/INT (when INTCN=1). When the A1IE bit is set to logic 0 or INTCN is set to logic 0, the A1F bit does not initiate the an interrupt signal. The A1IE bit is disabled (logic 0) when power is first applied.

Alarm 1 Interrupt is used for the time for next measurement.

A2IE (Alarm 2 Interrupt Enable)—When set to a logic 1, this bit permits the A2F bit in the status register to assert SQW/INT (when INTCN=1). When the A2IE bit is set to logic 0 or NTCN is set to logic 0, the A2F bit does not initiate an interrupt signal. The A2IE bit is disabled (logic 0) when power is first applied.

Alarm 2 is used for the regular status wake up.

6. AD-Converters 6.1. Setting ADC1 to ADC3 (AD7730)

MCLK=4.1952 MHz

Mode Register

MD2 MD1 MD0 Mode of Operation=0 0 1 Continuous Conversion Mode

MR12 (B/U)=1: Unipolar mode

MR7 (HIREF)=0: 2.5V reference (nominal)

MR6=0

MR5 MR4 (RN1 RN0)=11: Input Range 0 mV to +80 mV

MR3 (CLKDIS)=0

MR2 (BO)=0

Filter Register

FR23-FR12 (SF11-SF0)=0111 0000 0011 (704 H): Default Update Rate=57 Hz

FR11 FR10 (Zero)=0 0

FR9 (SKIP)=0

FR8 (FAST)=0

FR7 FR6 (ZERO)=0 0

FR5 (AC)=1

FR4 (CHP)=1

FR3 FR2 FR2 FR0 (DL3-DL0)=1 1 1 1: Default Delay=48.75 μs

DAC Register

DR7–DR6=0 0

DR5–DR0=0 0 0 0 0 0

6.2. Measure ADC 1-ADC 3

For both $R_C$ and $R_R$ on ADC1 to ADC3 Readout Scaling is:

$$R = \frac{V_{IN} \, [V]}{0{,}125 \, [A]} (1LSB = 38{,}147 n\Omega @ 80 \text{ mV range})$$

Sample 1000 dataset (17.5 s). Calculate Average value 6.3. Setting ADC0 (AD7734)

MCLK=6.144 MHz

I/O Port Register

IO7 IO6 (P0 P1): Read P0 and P1 levels

IO5 IO4 (P0DIR P1DIR)=1 0: P0 output and P1 input

IO3 (RDYFN)=1:RDY on enabled channels

IO2 IO1=0 0

IO0 (SYNC)=0: No SYNC operation

Channel Conversion Time Register

CT7 (Chop)=0: Chopping Disabled

CT6-CT0 (FW)=5 Ch: Default Update Rate=1008 Hz

Mode Register

MD7 MD6 MD5 Mode of Operation=0 0 1: Continuous Conversion Mode

MD4=0 (CLKDIS)

MD1 (24/16 BIT)=1: 24 bit mode

MD0 (CLAMP)=0:

Channel Setup Register

CH7 CH6 CH 5=0 0 0

CH4 (Stat OPT)=0: Status register of RDY

CH3 (ENABLE)=1: Channel in continuous conversion mode

CH3=0

CH1 CH0 (RNG1 RNG0)=0 0: Range±10V 6.4. Measure ADC0

6.4.1. Channel 0

For $I_{closed}$ on ADC0 channel 0 Readout Scaling is:

$$I_{closed} = \frac{V_{in} \, [V]}{5[\Omega]}; (LSB = 238 \text{ nA}@ \pm 10 \text{ V range})$$

Sample 4000 dataset (4s).

Calculate RMS Value.

6.4.2. Channel 1-3

For $U_{open}$ on ADC0 channel 1-3 Readout Scaling is:

$U_{open}=27.6 \cdot V_{in}$; ($LSB=32.92$ μV@±10V range)

Sample 4000 dataset (4s).
Calculate RMS Value.

7. Power Supplies

The board is supplied from an external 12V DC. Except from $3.3V_{Allways}$ (and $5V_{allways}$) all the supplies can be controlled by the CPU.

The supplies interacts as follows:

After start of each power supply, and delay time of 100 ms must be kept to ensure that the supply is stable, before a measurement starts.

The measurement sequence including power control is listed in Chapter 8.

TABLE 4

Interactions between supplies

| Name | CPU IF | Characteritics | | Supplies | | |
|---|---|---|---|---|---|---|
| 12 Vdc in | 12 V_Status (In) | External DC input | 5 Vcom | 3.3 Vcom | 5 Vallways | 3.3 Vallways |
| 3.3 V always | — | Linear regulator in IPM6220 | CPU | RS232 | EEPROM | |
| 5 V always | — | Linear regulator in IPM6220 | | | | |
| 3.3 Vcom | Power_Shut_Down (P36) | Non-isolated switched DC/DC converter (Buck) | Digital Isolation1-4 (primary side) | | | |
| 5 Vcom | | Non-isolated switched DC/DC converter (Buck) | $7V_0$-$7V_3$ | Probe relays # 1-3 | | |
| $7V_0$ | Power0_EN | Isolated non-regulated switched DC/DC converter | $5V_0$ | | | |
| $7V_1$ | Power1_EN | As $7V_0$ | $5V_1$ | | | |
| $7V_2$ | Power2_EN | As $7V_0$ | $5V_2$ | | | |
| $7V_3$ | Power3_EN | As $7V_0$ | $5V_3$ | | | |
| $5V_0$ | Power0_EN | Linear regulator | Digital Isolation0 (secondary side) | ADC0 (AD7734) | | |
| $5V_1$ | Power1_EN | Linear regulator | Digital Isolation1 (secondary side) | ADC1 (AD7730) | Excitation probe 1 | |
| $5V_2$ | Power2_EN | Linear regulator | Digital Isolation2 (secondary side) | ADC1 2 (AD7730) | Excitation probe 2 | |
| $5V_3$ | Power3_EN | Linear regulator | Digital Isolation3 (secondary side) | ADC3 (AD7730) | Excitation probe 3 | |

7.1. Control of Supplies

The CPU is supplied from 3.3V always supply. This is present as long as the DC input is powered. The CPU can control the other supplies.

Main Power

Main Power (3.3Vcom and 5Vcom) can be turned off setting the "Power_shut_down" port to a 0. Setting the port to a 1 turns on Main Power.

The main power gives a PGOOD (IRQ3) when it is ready. Start time for this power is approximately 25 ms.

Isolated Power Supplies

The Main Power must be turned on before any of the Isolated Power supplies are turned on.

Only one of the isolated power supplies must be turned on at a time.

Setting Power3_EN to a 1 turn on the power to the ADC3.
Setting Power3_EN to a 0 turn off the power to the ADC3
Setting Power2_EN to a 1 turn on the power to the ADC2.
Setting Power2_EN to a 0 turn off the power to the ADC2
Setting Power1_EN to a 1 turn on the power to the ADC1.
Setting Power1_EN to a 0 turn off the power to the ADC1
Setting Power0_EN to a 1 turn on the power to the ADC0.
Setting Power0_EN to a 0 turn off the power to the ADC0

7.2. Potentials

In order to have a corrosion that is representative to the corrosion in the pin holes of the gas pipe, the 3 probes must be kept at the same potential as the pipe most of the time. This is done by 3 relays when they are not asserted (Normally Closed). When measuring the resistance of the 2 elements in each probe, the relay is opened, and the input channel (ADC1-4) is floating.

Spread Resistance is measured by ADC0, and this is referring to the potential of the pipe. Measuring the 2 parameters $V_{open}$ and $I_{closed}$ is done on each probe by opening the relay to the probe and measuring $V_{open}$ for this probe on the ADC0 channel 1 to 4. $I_{closed}$ is measured on ADC0 channel 0. The relays decides on which probe $I_{closed}$ is measured. The 2 other relays must be open at this stage.

The CPU and RS232 are at all times isolated from all the 4 ADC channels and the pipe.

7.3. Power Monitor

The Input power can be measured at the AN5 ADC on the CPU. In order to reduce power consumption, this input has to enabled for reading and disabled again. Setting "Measure_DC_IN" at P73 to a 1, enables the monitor. Setting the port to a 0 disables the monitor.

The Inputsignal on AN5 must be scaled to: $V_{DC\ in}=6.49 \times V_{AN5}$

8. Measurement Sequence

The normal measuring sequence is as follows:
Wake from sleep mode on interrupt from RTC.
Enable Power monitor
Wait 1 ms
Read Power Monitor
Disable Power Monitor
Enable Main Power
Wait for PGOOD (25 ms)
Open Relay1
Open Relay2
Open Relay3
Enable Power0
Wait 100 ms
Setup ADC0
Measure ADC0 channel 1 ($V1_{open}$)
Close Relay1
Wait 100 ms
Setup ADC0
Measure ADC0 channel 0 ($I1_{closed}$)
Open Relay1
Wait 100 ms
Measure ADC0 channel 2 ($V2_{open}$)
Close Relay2
Wait 100 ms
Setup ADC0
Measure ADC0 channel 0 ($I2_{closed}$)
Open Relay2
Wait 100 ms
Measure ADC0 channel 3 ($V3_{open}$)
Close Relay3
Wait 100 ms
Setup ADC0
Measure ADC0 channel 0 ($I3_{closed}$)
Open Relay3
Disable Power0
Enable Power1
Wait 100 ms
Setup ADC1
Internal Full scale calibration ADC1
Internal Zero scale calibration ADC1
Measure ADC1 channel 2 ($R1_R$)
Measure ADC1 channel 1 ($R1_C$)
Disable Power1
Enable Power2
Wait 100 ms
Setup ADC2
Internal Full scale calibration ADC2
Internal Zero scale calibration ADC2
Measure ADC2 channel 2 ($R2_R$)
Measure ADC2 channel 1 ($R2_C$)
Disable Power2
Enable Power3
Wait 100 ms
Setup ADC3
Internal Full scale calibration ADC3
Internal Zero scale calibration ADC3
Measure ADC3 channel 2 ($R3_R$)
Measure ADC3 channel 1 ($R3_C$)
Disable Power3
Close Relay1
Close Relay2
Close Relay3
Save data
Set RTC Alarm register
Enable RTC Interrupt (IRQ6)
Shut down Main Power
Go to sleep mode 9. Related Documents ..\Software\Software Requirement Specification V010.doc
..\Requirement specification V030.doc
..\Design specification V031.doc
Calculations\Dimensionering Corrosion Detector V040.doc Annex 5

Translation into English of text in screen printout of FIG. 4:
This is an ER probe which is suitable for measurings on gas pipes (77 chr)

The invention claimed is:

1. A method of diagnosing corrosion risk of a pipe or a pipeline buried in soil due to DC stray currents and/or AC voltages induced in the soil, comprising:
  i) providing a two-part metal probe including a first probe part having a first metal element of a first size and a first specific resistivity $R_C$, said first probe part constituting an exposed element, and a second probe part having a second metal element of a second size and a second specific resistivity $R_R$, said second probe part constituting an environmentally isolated reference element;
  ii) burying said two-part metal probe in said soil;
  iii) electrically connecting said two-part metal probe to said pipe or pipeline;
  iv) measuring an AC current flowing between said pipe or said pipeline and said two-part metal probe while said pipe or said pipeline and said two-part metal are electrically connected;
  v) electrically disconnecting said two-part metal probe from said pipe or pipeline;
  vi) measuring an AC voltage between said pipe or pipeline and said two-part metal probe while said pipe or pipeline and said two-part metal probe are disconnected from one another;
  vii) measuring a spread resistance based on said AC current determined in step iv) and said AC voltage measured in step vi) according to Ohm's Law;
  viii) passing a first excitation current through said first probe part and determining the voltage generated by said first excitation current across said first probe part for measuring the resistance of said first probe part according to Ohm's Law while said pipe or pipeline and said two-part metal probe are disconnected from one another;
  ix) passing a second excitation current through said second probe part and determining the voltage generated by said second excitation current across said second probe part for measuring the resistance of said second probe part according to Ohm's Law while said pipe or pipeline and said two-part metal probe are disconnected from one another;
  x) storing said measurements provided in steps iv), vi), vii), viii), and ix);
  xi) repeating said steps iii) through x) periodically,
  xii) determining an actual corrosion of said first probe part based on the measurements performed in steps viii) and ix) according to a mathematical corrosion algorithm; and
  xiii) diagnosing the risk of corrosion of said pipe or pipeline based on an empirical combination of the actual corrosion of said first probe part, said spread resistance determined in step vii) and said AC voltage measured in step vi).

2. The method according to claim 1, said first probe part and said second probe part having identical metal elements.

3. The method according to claim 1, said step xii being performed in accordance with the following equation:

$$\sigma(t) = \sigma(t=0) \cdot \frac{R_R(t)}{R_C(t)} \cdot \frac{R_C(t=0)}{R_R(t=0)}$$

in which σ(t) denotes thickness of an element as a function of time.

4. The method according to any of the claims 1-3, said diagnosing of step xiii being performed in accordance with the following table:

| Event | Active corrosion | Spread resistance | AC voltage | Diagnose |
|---|---|---|---|---|
| 1 | No | high (1-10 Ωm²) | low (below approx. 10 V) | No risk |
| 2 | No | high (1-10 Ωm²) | high (above approx. 10 V) | No critical condition but monitor spread resistance further |
| 3 | No | low (0.001-0.1 Ωm²) | low (below approx. 10 V) | No critical condition but be aware of increased AC voltage |
| 4 | No | low (0.001-0.1 Ωm²) | high (above approx. 10 V) | Risk of AC corrosion incubation period |
| 5 | Yes | low (0.001-0.1 Ωm²) | high (above approx. 10 V) | AC corrosion - take mitigation actions |
| 6 | Yes | low (0.001-0.1 Ωm²) | low (below approx. 10 V) | Corrosion may arise from DC stray current |
| 7 | Yes | high (1-10 Ωm²) | low (below approx. 10 V) | Corrosion may arise from DC stray current |
| 8 | Yes | high (1-10 Ωm²) | high (above approx. 10 V). | Corrosion may arise from DC stray current |

5. The method according to claim 4, wherein said spread resistance is high if the value of said spread resistance is above 1 Ohm, and low if the value of the spread resistance is below 0.1 Ohm.

6. The method according to claim 4, wherein said AC voltage is high if said voltage is higher than 10V.

7. The method according to any of the claims 1-3, said steps iii through x being repeated with a frequency of one or more days.

8. A system for diagnosing corrosion risk of a pipe or a pipeline buried in soil due to DC stray currents and/or AC voltages induced in the soil, comprising:

i) a two-part metal probe including a first probe part having a first metal element of a first size and a first specific resistivity, said first probe part constituting an exposed element, and a second probe part having a second metal element of a second size and a second specific resistivity, said second probe part constituting an environmentally isolated reference element;

ii) a switching device for the selective electrical connection and disconnection of said two-part metal probe and said pipe or pipeline;

iii) a measuring apparatus electrically connected to said two-part metal probe and including:

an AC current measuring circuit for measuring an AC current flowing between a pipe or pipeline and the two-part metal probe when said probe is buried in said soil while said two-part metal probe is electrically connected to said pipe or pipeline;

an AC voltage measuring circuit for measuring an AC voltage between said pipe or said pipeline and said two-part metal probe when said two-part metal probe is buried within said soil while said two-part metal probe is electrically disconnected from said pipe or pipeline;

a resistance measuring circuit connected to said AC current measuring circuit and said AC voltage measuring circuit for determining a spread resistance based on Ohm's Law;

a current excitation circuit for (a) passing through said cable a first excitation current to said first probe part while said pipe or pipeline and said two-part metal probe are disconnected from one another; (b) for measuring the voltage generated by said first excitation current across said first probe part for measuring the resistance of said first probe part according to Ohm's Law; (c) for passing a second excitation current through said cable to said second probe part while said pipe or pipeline and said two-part probe are disconnected from one another; and (d) for determining the voltage generated by said second excitation current across said second probe part for measuring the resistance of said second probe part according to Ohm's Law;

a data processor for determining an actual corrosion of said first probe part based on the measured resistances of the first and second probe parts according to a mathematical corrosion algorithm;

a storage device for storing the measurements made by said AC current measuring circuit, said AC voltage measuring circuit, said spread resistance measuring circuit and said current excitation circuit; and a diagnosing circuit for diagnosing the risk of corrosion of said pipe or pipeline based on an empirical combination of the actual corrosion of said first probe part, said spread resistance and said AC voltage.

9. The system according to claim 8, wherein said measuring apparatus includes a micro processor constituting part of said AC current measuring circuit, said AC voltage measuring circuit, said spread resistance measuring circuit, said current excitation circuit, said storing circuit, and said diagnosing circuit, said micro processor controlling the overall operation of the apparatus for periodically repeating the measurements.

10. The system according to any of the claims 8 or 9, wherein said measuring apparatus includes two or more cable connectors for establishing connections to two or more two-part metal probes.

11. The system according to any of the claims 8-9, wherein said measuring apparatus further includes a data connector configured for connecting to an external device operable for receiving information regarding said two-part metal probe.

* * * * *